United States Patent
Sennlaub et al.

(10) Patent No.: US 10,519,232 B2
(45) Date of Patent: Dec. 31, 2019

(54) AGENTS FOR USE IN THE TREATMENT OF RETINAL INFLAMMATION

(71) Applicants: Sorbonne Universite, Paris (FR); CENTRE NATIONAL DE LA RECHERCHE SCIENTIFIQUE (CNRS), Paris (FR)

(72) Inventors: Florian Sennlaub, Paris (FR); Xavier Guillonneau, Boulogne Billancourt (FR); Olivier Levy, Paris (FR); José-Alain Sahel, Paris (FR)

(73) Assignees: SORBONNE UNIVERSITE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/111,986

(22) PCT Filed: Jan. 22, 2015

(86) PCT No.: PCT/EP2015/051293
§ 371 (c)(1),
(2) Date: Jul. 15, 2016

(87) PCT Pub. No.: WO2015/110556
PCT Pub. Date: Jul. 30, 2015

(65) Prior Publication Data
US 2016/0340424 A1  Nov. 24, 2016

(30) Foreign Application Priority Data
Jan. 22, 2014 (EP) .................................... 14152189

(51) Int. Cl.
| *A61K 39/395* | (2006.01) |
| *A61K 38/00* | (2006.01) |
| *C07K 16/24* | (2006.01) |
| *C07K 16/28* | (2006.01) |

(52) U.S. Cl.
CPC ........ *C07K 16/248* (2013.01); *C07K 16/2866* (2013.01); *C07K 2317/76* (2013.01)

(58) Field of Classification Search
None
See application file for complete search history.

(56) References Cited

U.S. PATENT DOCUMENTS

| 5,210,075 A | 5/1993 | Scholz et al. |
| 6,001,962 A | 12/1999 | Ramer et al. |
| 6,846,637 B1 | 1/2005 | Chiodi |
| 2011/0136794 A1* | 6/2011 | Kawashima ......... C07D 207/34 514/224.2 |
| 2013/0195806 A1* | 8/2013 | Gay ..................... A61K 45/06 424/93.7 |

FOREIGN PATENT DOCUMENTS

| EP | 0628639 | 12/1994 |
| EP | 1990060 | 11/2008 |
| EP | 2116530 A1 | 11/2009 |
| JP | H02188600 | 7/1990 |
| JP | H07324097 | 12/1995 |
| JP | H08311098 | 11/1996 |
| WO | 9219759 | 11/1992 |
| WO | 9617869 | 6/1996 |
| WO | 9618648 | 6/1996 |
| WO | 2004045507 A2 | 6/2004 |
| WO | 2013148183 | 10/2013 |
| WO | WO 2014/074905 | * 5/2014 ............. C07K 16/24 |

OTHER PUBLICATIONS

Rodrigues 2007. Ophthalmologica. 221:143-152.*
Scheller et al. 2011. BBA 1813:878-888 (Year: 2011).*
International Search Report issued in PCT/EP2015/051293, dated Mar. 26, 2015.
Written Opinion of the International Searching Authority issued in PCT/EP2015/051293, dated Mar. 26, 2015.
Brakenhoff et al. "Development of a human interleukin-6 receptor antagonist" J. Biol. Chem., 1994, 269(1):86-93.
Camelo et al. "Delta-like 4 inhibits choroidal neovascularization despite opposing effects on vascular endothelium and macrophages" Angiogenesis, 2012, 15(4):609-622.
Combadiere et al. "Decreased atherosclerotic lesion formation in CX3CR1/apolipoprotein E double knockout mice" Circulation, 2003, 107(7):1009-1016.
Greaney et al. "A Fas agonist induces high levels of apoptosis in haematological malignancies" Leukemia research, 2006, 30(4):415-426.
Gupta et al. "Activated microglia in human retinitis pigmentosa, late-onset retinal degeneration, and age-related macular degeneration" Exp. Eye Res. 2003, 76(4):463-471.
Hirata et al. "Characterization of IL-6 receptor expression by monoclonal and polyclonal antibodies" J. Immunol., 1989, 143(9):2900-2906.
Houssier et al. "CD36 deficiency leads to choroidal involution via COX2 down-regulation in rodents" PLoS Med, 2008, 5(2):e39.
Klein et al. "Fifteen-year cumulative incidence of age-related macular degeneration: the Beaver Dam Eye Study" Opthalmology, 2007, 114(2): 253-262.
Klein et al. "Inflammation, complement factor h, and age-related macular degeneration: the Multi-ethnic Study of Atherosclerosis" Ophtalmology, 2008: 115(10), 1742-1749.

(Continued)

*Primary Examiner* — Shulamith H Shafer
(74) *Attorney, Agent, or Firm* — Heslin Rothenberg Farley & Mesiti P.C.

(57) ABSTRACT

The present invention relates to preventive and/or therapeutic agents for use in the treatment of retinal inflammation, and more specifically of Age-related macular degeneration and Retinitis pigmentosa, wherein said agents are selected from an IL-6 inhibitor, an APOE inhibitor and/or a Fas activator as an active ingredient.

8 Claims, 10 Drawing Sheets

(56) References Cited

OTHER PUBLICATIONS

Kohno et al. "Photoreceptor proteins initiate microglial activation via Toll-like receptor 4 in retinal degeneration mediated by all-trans-retinal" J. Biom. Chem. 2013, 288(21):15326-15341.

Ma et al. "Contribution of IL-17-producing gamma delta T cells to the efficacy of anticancer chemotherapy" J. Exp. Med., 2011, 208(3), 491-503.

Matsuda et al. "Establishment of an interleukin 6 (IL 6)/B cell stimulatory factor 2-dependent cell line and preparation of anti-IL 6 monoclonal antibodies" Eur. J. immunol., 1988, 18(6): 951-956.

Sato et al. "Humanization of an anti-human IL-6 mouse monoclonal antibody glycosylated in its heavy chain variable region" Hum. Antibodies Hybridomas, 1996; 7(4):175-183.

Savino et al. "Generation of interleukin-6 receptor antagonists by molecular-modeling guided mutagenesis of residues important for gp130 activation" EMBO J., 1994, 13(6):1357-1367.

Seddon et al. "Progression of age-related macular degeneration: prospective assessment of C-reactive protein, interleukin 6, and other cardiovascular biomarkers" Arch. Ophtalmol 2005, 123(6):774-782.

Sennlaub et al. "CCR2(+) monocytes infiltrate atrophic lesions in age-related macular disease and mediate photoreceptor degeneration in experimental subretinal inflammation in Cx3cr1 deficient mice" EMBO Mol. Med., 2013, 5(11):1775-1793.

Tamura et al. "Soluble interleukin-6 receptor triggers osteoclast formation by interleukin 6" Proc. Natl. Acad. Sci. USA, 1993, 90(24):11924-11928.

Verbrugge et al. "Combining radiotherapy with APO010 in cancer treatment" Clin. Cancer Res. 2009, 15(6):2031-38.

Yu et al. "Epigenetic signature and enhancer activity of the human APOE gene" Hum. Mol. Genet, 2013, 22(24):5036-47.

* cited by examiner

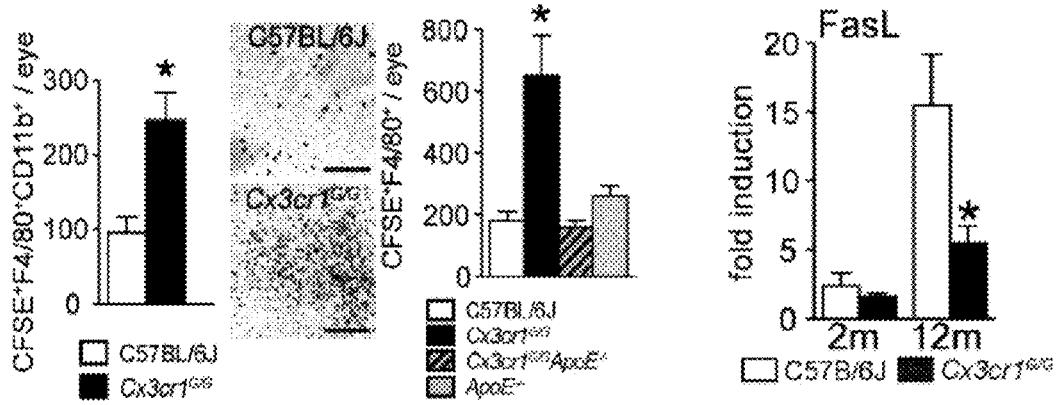
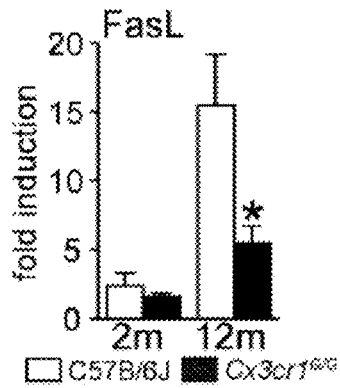
FIG. 11
FIG. 12
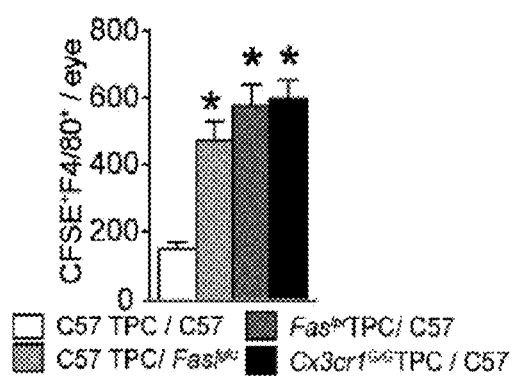
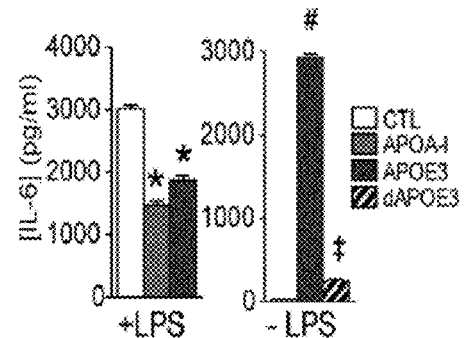
FIG. 13
FIG. 14
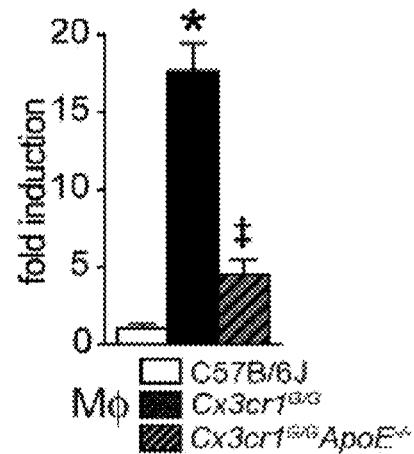
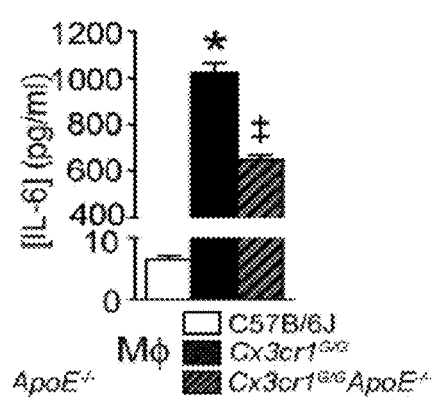
FIG. 15
FIG. 16

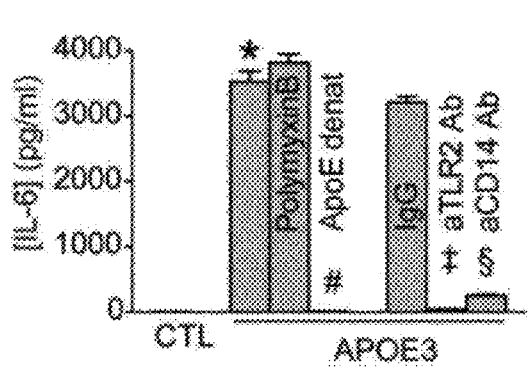 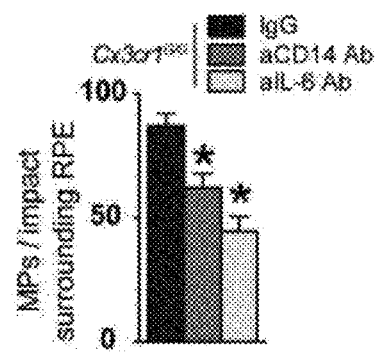
FIG. 39　　　　　　　　FIG. 40
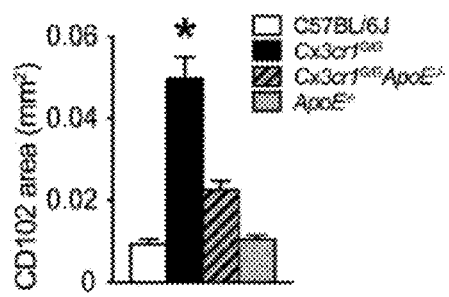 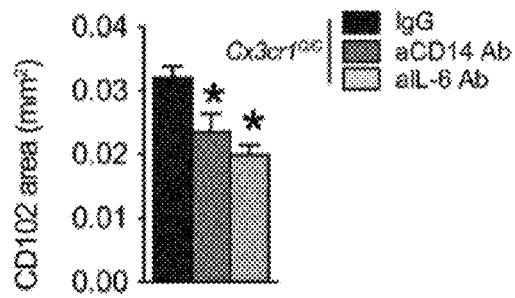
FIG. 41　　　　　　　　FIG. 42
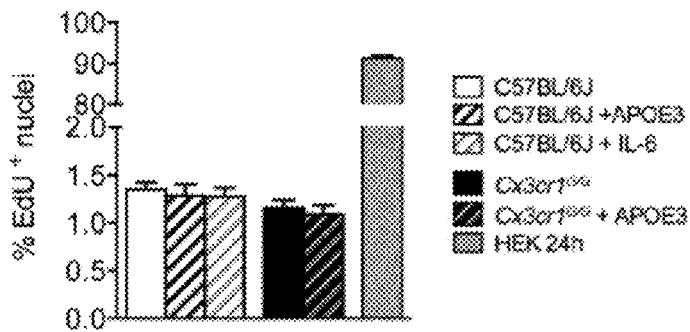
FIG. 43

AGENTS FOR USE IN THE TREATMENT OF RETINAL INFLAMMATION

CROSS REFERENCE TO RELATED APPLICATIONS

This application is a national stage filing under section 371 of International Application No. PCT/EP2015/051293, filed on Jan. 22, 2015, and published on Jul. 30, 2015 as WO/2015/110556, and claims priority to European Application No. 14152189.8, filed on Jan. 22, 2014. The entire disclosures of each of the prior applications are hereby incorporated herein by reference.

FIELD OF INVENTION

The present invention relates to preventive and/or therapeutic agents for use in the treatment of retinal inflammation, and more specifically of Age-related macular degeneration and Retinitis pigmentosa.

BACKGROUND OF INVENTION

Age related macular degeneration (AMD) is the leading cause of legal blindness in the developed world and the most common geriatric eye disorder. AMD is characterized by degeneration of the neuroepithelium in the macular area of the eye. Two main advanced forms of AMD may be distinguished: neovascular AMD and atrophic AMD.

Neovascular AMD, also referred to as "exsudative" or "wet" AMD is characterized by the invasion of abnormal choroidal (or occasionally retinal) blood vessels and fluid leakage into the retina, a phenomenon also referred to as "choroidal neovascularization" or "CNV". Neovascular AMD is the leading cause of blindness among the elderly in industrialized nations and several treatments were developed and shown to improve the clinical situation of the treated patients, especially through therapies targeting VEGFA, a potent stimulator of angiogenesis and vasopermeability.

Atrophic AMD, also referred to as "geographic atrophy" or "GA", "end-stage dry" AMD or "dry" AMD, affects the macula area, in which the retinal pigmented epithelium can no longer support photoreceptor function owing to spontaneous degeneration of large confluent regions. The incidence of atrophic AMD and neovascular AMD are comparable, but the expansion of the atrophic lesions and associated visual impairment is usually a slower process. No currently approved therapies are available to this date for preventing or curing geographic atrophy, mainly as a result of the lack of identification of suitable molecular targets. Some studies have demonstrated that consumption of vitamin E and C, of betacaroteinoids and Zinc may slow the development of atrophic DMLA, but the progression of the disease is unfortunately not stopped.

Several studies have established that the subretinal space located between the retinal pigmented epithelium and the photoreceptor outer segments is a zone of immune privilege mediated by immunosuppressive retinal pigmented epithelium signals. Nevertheless, mononuclear phagocytes (comprising a family of cells that include microglial cells, monocytes and macrophages) were shown to accumulate in the subretinal space in the advanced forms of sight-threatening AMD: i.e. CNV and geographic atrophy. Whereas subretinal migration of microglial cells appear to be required for eliminating visual by-products and to maintain vision, the accumulation thereof as well as of macrophages in the subretinal space was purported to result in a destructive inflammation possibly involved in AMD development (Gupta et al., 2003. and Kohno et al., 2013).

Further, increased levels of inflammation mediator proteins such as interleukin 6 (IL-6) have been measured in the serum of patients suffering from AMD (Klein et al., 2008 and Seddon et al., 2005). Nevertheless, these studies failed to identify or even suggest specific molecular targets for preventing and/or treating AMD, and more specifically atrophic AMD. Whereas EP 1 990 060 has disclosed the use of IL-6 antagonists for treating the neovascular form of AMD, this document contains no indication nor suggestion that IL-6 antagonists might exert any beneficial effect on patients suffering from the atrophyic form of AMD. In addition, WO2004/045507 discloses the use if IL-6 antagonists for treating diseases/conditions associated with pathological angiogenesis, such as for example wet AMD, since this disease is characterized by an abnormal development of choroidal neovascularization. By no mean, WO2004/045507 can be regarded as describing treatment of dry AMD, since it does not rely to neovascularization deficiencies or abnormalities. Similarly, EP2116530 discloses a novel pyrrole derivative having an inhibitory activity against IL-6 production and/or inhibitory effect on choroidal neovascularization, and by no mean relates to the treatment of diseases not involving neoangiogenesis, such as dry AMD.

Methods for treating drusen comprising administering active ingredients such as imatinib mesylate, ponatinib, bosutanib, DAPT and bexarotene are also disclosed in WO2013/148183. Drusen are extracellular deposits that accumulate between the retinal pigmented epithelium and the Bruch membrane. They are composed of aggregated intracellular, extracellular and secreted proteins, and lipids and cellular components. As demonstrated in WO2013/148183, APOE notably amounts within the major components of human drusen. WO2013/148183 suggests that treating cells with the above listed active ingredients results in a decrease of APOE levels, among others, in drusen, and establishes a link between the treatment of drusen and the treatment of atrophic AMD. Nevertheless, this document actually fails to demonstrate unambiguously that an actual effect of the tested active ingredients is obtained on APOE expression and accumulation in drusen. Further, the causal relationship established between atrophic AMD and drusen in this document is clearly invalidated by several publications within this field (see for instance Klein et al., 2007, which demonstrates that drusen may only be regarded as providing an increased risk to develop AMD, but should in no manner be considered as a symptom of atrophic AMD).

In view of these elements, there is therefore still an ongoing need for identifying active ingredients for preventing and/or treating retinal inflammation, and more particularly atrophic AMD.

This objective is reached by the present invention, since the inventors have surprisingly demonstrated that increased amounts of APOE induce IL-6 expression, which in turn downregulates the reticulum pigmented epithelium-expressed FasL. The inventors demonstrated that diminished FasL expression then enables prolonged subretinal mononuclear phagocytes survival, age-dependent mononuclear phagocyte accumulation, and associated photoreceptor degeneration. These findings revealed a pro-inflammatory function of APOE, which is in total contrast with its well-known anti-inflammatory role in other pathological contexts. Inventors have thus surprisingly established that inhibiting excess APOE and IL-6 in retinal inflammation and more particularly in dry AMD and retinitis pigmentosa results in preventing and/or curing the inflammation and thereby preventing the photoreceptor degeneration.

SUMMARY

This invention thus relates to a preventive and/or therapeutic agent for use in the treatment of retinal inflammation wherein said preventive and/or therapeutic agent comprises an IL-6 inhibitor, an APOE inhibitor and/or a Fas activator as an active ingredient.

In a particular embodiment of the present invention, the said retinal inflammation comprises atrophic age-related macular degeneration (atrophic AMD) and retinitis pigmentosa. In a preferred embodiment, the invention relates to a preventive and/or therapeutic agent for use in the treatment of atrophic age-related macular degeneration (atrophic AMD).

In a particular embodiment, the said IL-6 inhibitor for use in the invention comprises (i) an antagonist of IL-6 activity, such as an antibody recognizing IL-6, a soluble IL-6 receptor or an inhibitor of IL-6 translation or (ii) an antagonist of IL-6 receptor, such as an antibody recognizing IL-6R or an IL-6R binding peptide.

In a particular embodiment, the said APOE inhibitor for use in the invention comprises an antibody directed against APOE, an inhibitor of APOE translation or a soluble APOE receptor or a functional fragment thereof.

In an embodiment of the invention, the said Fas activator comprises a Fas agonist, such as FasL or functional fragments thereof, or FasL-mimicking peptides.

In an embodiment of the invention, the said preventive and/or therapeutic agent is delivered intra-vitreously.

In an embodiment of the invention, the said preventive and/or therapeutic agent comprises an IL-6 inhibitor and/or an APOE inhibitor, each in a concentration of from 5 mg/mL to 500 mg/mL.

DETAILED DESCRIPTION

The present invention relates to a preventive and/or therapeutic agent for use in the treatment of retinal inflammation wherein said preventive and/or therapeutic agent comprises an IL-6 inhibitor, an APOE inhibitor and/or a Fas activator as an active ingredient.

Within the meaning of the invention, by "retinal inflammation", it is meant an inflammation of the subretinal space mediated by mononuclear phagocytes. In a particular embodiment of the invention, the said retinal inflammation comprises atrophic age-related macular degeneration (atrophic AMD) and retinitis pigmentosa. According to another embodiment of the invention, the expression "retinal inflammation" comprises atrophic age related degeneration and retinitis pigmentosa, but does not comprise choroidal neovascularization or neovascular AMD. In a particular embodiment of the invention, the said preventive and/or therapeutic agent is thus used for treating atrophic age-related macular degeneration and retinitis pigmentosa, but not choroidal neovascularization. In another embodiment, the said preventive and/or therapeutic agent of the invention is not used for treating wet AMD and diseases related to neovascularization. In a preferred embodiment of the invention, the said preventive and/or therapeutic agent is used for treating atrophic age-related macular degeneration.

In a particular embodiment of the present invention, the preventive and/or therapeutic agent comprises an IL-6 inhibitor.

IL-6 is a cytokine also known as "B-cell stimulating factor 2" (BSF2) or interferon β2, which is known to exert its biological activity through the binding of its specific IL-6 receptor (a 80 KDa protein).

Within the meaning of the invention, by "IL-6 inhibitor", it is thus meant substances that blocks IL-6-mediated transduction signal and inhibits IL-6 biological activity, either in inhibiting directly IL-6 or through the inhibition of its IL-6 receptor (IL-6R) activity.

IL-6 direct inhibitors include but are not limited to: antibodies or antibody fragments directed against IL-6 or fragments thereof, proteins or peptides capable to bind IL-6 within conditions where IL-6 is no more able to bind the IL-6 receptor, or siRNAs or ASOs directed against IL-6 gene and/or transcript. IL-6 direct inhibitors may further comprise soluble IL-6 receptors or fragments thereof that have preserved their capacity to bind IL-6 and to compete with the natural IL-6 receptor.

Inhibitors of IL-6 receptor include but are not limited to antibodies directed against IL-6 receptor or fragments thereof, IL-6 variants, IL-6 fragments or IL-6 peptidomimetic compounds that have preserved their capacity to bind IL-6 receptor and/or to compete with IL-6 for binding IL-6 receptors, but that have lost their ability to promote signal transduction through the binding of IL-6 receptor. Inhibitors of IL-6 receptor may further comprise siRNAs or ASOs directed against the gene and/or the transcript of the IL-6 receptor gene.

In a particular embodiment, antibodies directed against IL-6 for use in the present invention preferably include MH166 antibody (Matsuda. T. et al., 1988), SK2 antibody or a humanized derivative thereof (Sato et al. 1996), Siltumab (Jansson Research), Avimer TM C326 (Avidia), Sirukumab and Siltuximab (Centocor Inc.), Olokizumab (UVB Inc.), ALD518 (Bristol-Myers Squibb), VX30 (Vaxinex), ARGX-109 (arGen-X BV) and FM101 (Femta Pharmaceuticals). Preferably, the anti-IL-6 antibody MAB 406 is contemplated for use in the present invention (Ma et al. 2011).

In a particular embodiment, antibodies directed against IL-6 receptor for use in the present invention preferably include MR16-1 antibody (Tamura, T. et al., 1993); PM-1 antibody (Hirata et al., 1989); AUK12-20 antibody, AUK64-7 antibody and AUK146-15 antibody (WO92/19759).

In a particular embodiment, IL-6 variants for use in the present invention preferably include those described in Brakenhoff et al., 1994, Savino et al. 1994, WO 96/18648 and WO 96/17869, as well as antibodies known under the name Sarilumab (Regeneron), Tocilizumab (Chugai, Roche) and FE301 (Conaris/Ferring).

In a particular embodiment, IL-6 partial peptides and IL-6 receptor partial peptides for use in the present invention preferably include those described in JP-A (Kokai) H02-188600, JP-A (Kokai) H07-324097, JP-A (Kokai) H08-311098, and U.S. Pat. No. 5,210,075.

In a particular embodiment, soluble IL-6 receptor for use in the present invention preferably essentially consists of the extracellular region of the cell membrane-bound IL-6 receptor and differs from the latter in that it lacks the transmembrane and intracellular regions.

In a particular embodiment of the present invention, the preventive and/or therapeutic agent comprises an APOE inhibitor.

Apolipoprotein E (or "ApoE") is a class of 299 amino acids long apolipoprotein found in the chylomicron and Intermediate-density lipoprotein (IDLs) that is essential for the normal catabolism of triglyceride-rich lipoprotein constituents. ApoE is polymorphic: three major isoforms are identified, namely APOE2, APOE3 and APOE4, differing from each other by only one or two amino acids. Nevertheless, these differences appear to alter both APOE structure and function.

Within the meaning of the invention, by "APOE inhibitor", it is thus meant substances that inhibit APOE biological activity, either in inhibiting directly APOE or through the inhibition of its activity through receptors or via its interaction with cholesterol rich lipid rafts, in which receptors are located.

APOE direct inhibitors include but are not limited to: antibodies directed against APOE or fragments thereof, proteins or peptides capable to bind APOE within conditions where APOE is no more able to bind lipids (eg. Cholesterol) and/or the APOE receptor or siRNAs or ASOs directed against APOE gene and/or transcript. APOE direct inhibitors may further comprise soluble APOE receptors or fragments thereof that have preserved their capacity to bind APOE and to compete with the natural APOE receptor or with its capacity to bind lipids.

Inhibitors of APOE receptor include but are not limited to antibodies directed against APOE receptor or fragments thereof, APOE variants. APOE fragments or APOE peptidomimetic compounds that have preserved their capacity to bind APOE receptor and/or to compete with APOE for binding lipids and/or the APOE receptors, but that have lost their ability to promote signal transduction through the APOE receptor binding. Inhibitors of APOE receptor may further comprise siRNAs or ASOs directed against the gene and/or the transcript of the APOE receptor gene.

Within the meaning of the invention, by "APOE", it is meant whole or part of the isoforms of APOE, i.e. at least one, preferably at least two, even more preferably at least three of the APOE isoforms selected in the group of APOE2, APOE3 and APOE4.

In a particular embodiment, APOE inhibitors for use in the present invention are anti-APOE antibodies, such as AB947 (Millipore), NB110-60531 (Novus Biologicals), LS-B6780/43356 (Lifespan Bioscience) and EP1373Y (Epitomics).

In a particular embodiment, APOE4-specific antibodies for use in the present invention preferably include those commercially available under the names ApoE4 Antibody (Bio Vision), Apolipoprotein E4 antibody (MBL International), Apo-E4 (5G7) monoclonal antibody (Covance), Apo-E4 (9D11) monoclonal antibody (Covance), and ApoE4 (5B5) anti-human mouse IgG MoAb (IBL-America (Immuno-Bio logical Laboratories)).

Further, in a particular embodiment of the present invention, the APOE inhibitor is a soluble receptor for LDL (LDLR), such as the recombinant human LDL R 2148-LD/ CF (R&D SYSTEMS).

In a particular embodiment of the present invention, the preventive and/or therapeutic agent comprises a Fas activator.

Fas is also known as FAS receptor (or FasR), as apoptosis antigen 1 (APO-1 or APT), cluster of differentiation 95 (CD95) or tumor necrosis factor receptor superfamily member 6 (TNFRSF6), corresponds to a death cell receptor located on the surface of cells which, upon activation, can trigger programmed cell death (apoptosis). Activation of Fas through the binding of Fas ligand (FasL) notably induces the formation of the death-inducing signaling complex (DISC).

Within the meaning of the invention, by "Fas activator", it is meant substances that are capable to activate Fas biological activity, such as to induce the onset of the apoptotic pathway.

Fas activators include but are not limited to: proteins and peptides capable to bind Fas and to activate the formation of DISC, as well as FasL variants, fragments or peptidomimetics that have retained the capacity of FasL to bind Fas and to trigger the apoptosis of the corresponding cells.

In a particular embodiment, Fas activators for use in the present invention preferably include the FasL ligand or any functional fragment or derivative thereof.

In a particular embodiment, Fas activators for use in the present invention preferably include the Fas receptor agonist APOO1O (TopoTarget, Copenhagen, Denmark), which is a recombinant, soluble, hexameric fusion protein consisting of three human Fas ligand (FasL) extracellular domains fused to the dimerforming collagen domain of human adiponectin with potential pro-apoptotic and antincoplastic activities. Fas receptor agonist APOO1O activates the Fas receptor, resulting in caspase dependent apoptosis in susceptible tumor cell populations (Verbrugge et al. 2009). In a particular embodiment. Fas activators for use in the present invention preferably include the Fas-agonist Mega FasL (Adipo-Gen). Further, additional Fas activators for use in the present invention preferably include Fas agonist peptides disclosed in U.S. Pat. Nos. 6,001,962 and 6,846,637.

Within the meaning of the invention, by "antibody fragment", it is meant any binding protein obtained from an antibody, and include for instance, but are not limited to, Fab, F(ab')2, Fv fragments as well as single chain Fv (ScFv), in which the Fvs on the H and L chains are linked via an appropriate linker, diabodies, triabodies, CDR1, CDR2, CDR3, combinations of CDR's, variable regions, tetrabodies, bifunctional hybrid antibodies, framework regions, constant regions, and the like.

Within the meaning of the invention, by "siRNA" or "small interference RNA", it is meant a double stranded structure containing from about 15 to about 50 base pairs, for example from about 21 to about 25 base pairs, and having a nucleotide sequence identical or nearly identical to an expressed target gene or RNA within the cell. The siRNA comprise a sense RNA strand and a complementary antisense RNA strand annealed together by standard Watson-Crick base-pairing interactions. The sense strand comprises a nucleic acid sequence which is substantially identical to a nucleic acid sequence contained within the target miRNA molecule. "Substantially identical" to a target sequence contained within the target mRNA refers to a nucleic acid sequence that differs from the target sequence by about 3% or less. The sense and antisense strands of the siRNA can comprise two complementary, single-stranded RNA molecules, or can comprise a single molecule in which two complementary portions are base-paired and are covalently linked by a single-stranded "hairpin" area. siRNA can be produced chemically or biologically, or can be expressed from a recombinant plasmid or viral vector through methods well-known to the one of skill in the art.

Within the meaning of the invention, by "Antisense oligonucleotides" (or "ASOs") it is meant small deoxyoligonucleotides with a sequence complementary to the mRNA of the target gene. These oligonucleotides bind to the target mRNA through complementary base-pairing and attract the binding of RNase H, an enzyme that degrades double strand RNA, thus destroying the target mRNA.

In an embodiment of the invention, the preventive and/or therapeutic agent is delivered intraocularly. Within the meaning of the invention, by "intraocular administration" it is meant an injection of the agent directly in the interior of the eye, wherein the interior of the eye means any area located within the eyeball, and which generally includes, but is not limited to, any functional (e.g. for vision) or structural tissues found within the eyeball, or tissues or cellular layers that partially or completely line the interior of the eyeball. Specific examples of such areas include the anterior chamber, the posterior chamber, the vitreous cavity, the choroid, the macula, and the retina, and blood vessels and nerves which vascularize or innervate a posterior ocular region or site. In one embodiment, interior of the eye means the posterior segment of the eye, including the posterior chamber, the vitreous cavity, the choroid, the macula, and the retina, and blood vessels and nerves which vascularize or innervate a posterior ocular region or site. According to this embodiment, the intraocular administration refers to an administration within the posterior segment of the eye, preferably within the vitreous, and the intraocular administration is preferably an intravitreal injection.

According to another embodiment, the administration route may be a topical ocular administration, such as, for example, the administration of eye drops or by bathing the eye in an ophthalmic solution comprising the composition or the kit of part of the invention.

According to an embodiment, the preventive and/or therapeutic agent is formulated in a form adapted for injection, preferably selected from the group comprising solutions, such as, for example, sterile aqueous solutions, dispersions, emulsions, suspensions, solid forms suitable for using to prepare solutions or suspensions upon the addition of a liquid prior to use, such as, for example, powder, liposomal forms and the like.

In an embodiment of the invention, the preventive and/or therapeutic agent comprises an IL-6 inhibitor and/or an APOE inhibitor in a respective concentration of from 5 mg/mL to 500 mg/mL, from 5 mg/mL to 100 mg/mL, from 5 mg/mL to 10 mg/mL.

In another embodiment of the invention, the preventive and/or therapeutic agent comprises an IL-6 inhibitor and/or an APOE inhibitor in a respective concentration from 1 μg/mL to 1 mg/mL, from 1 μg/mL to 500 μg/mL, 1 μg/mL to 100 μg/mL.

In another embodiment of the invention, the preventive and/or therapeutic agent comprises an IL-6 inhibitor and/or an APOE inhibitor in an intraocular concentration of 1 to 10 μg/mL of human intraocular liquid, preferably 5 μg/mL of human intraocular liquid.

BRIEF DESCRIPTION OF THE DRAWINGS

FIG. 11 is a histogram showing the quantification of subretinal CFSE$^+$F4/80$^+$ macrophages on Retinal pigment epithelium and retinal flatmounts 24 h after subretinal injections of CFSE$^+$ TPCs from C57BL/6J, Cx3cr1$^{GFP/GFP}$, Cx3cr1$^{GFP/GFP}$ApoE$^{-/-}$, and ApoE$^{-/-}$ mice into C57BL/6J mice and of C57BL/6J CFSE$^+$ TPCs into C57BL/6J with exogenously added APOE3 (calculated intraocular concentrations; n=8-20 per group, *ANOVAB C57BL/6J vs. Cx3cr1$^{GFP/GFP}$ and Cx3cr1$^{GFP/GFP}$ vs. Cx3cr1$^{GFP/GFP}$ApoE$^{-/-}$ p<0.0001; *MWt Cx3cr1$^{GFP/GFP}$ vs. Cx3cr1$^{GFP/GFP}$ p=0.0006; ‡ ANOVAD each group vs. C57BL/6J p<0.0001).

FIG. 12 is a histogram showing the levels of FasL mRNA measured by quantitative RT-PCR and normalized with β-actin mRNA of 2 months- and 12 months-old C57BL/6 and Cx3cr1$^{GFP/GFP}$ Retinal pigment epithelium/choroid plexus (n=6 per group, *MWt at 12 months p=0.0129).

FIG. 13 is a histogram showing the quantification of subretinal CFSE$^+$F4/80$^+$ macrophages on Retinal pigment epithelium and retinal flatmounts 24 h after subretinal injections of C57BL/6J CFSE$^+$ TPCs into C57BL/6J and Fas$^{gld/gld}$ mice and Cx3cr1$^{GFP/GFP}$ and Fas$^{lpr/lpr}$ TPCs into C57BL/6J mice (n=11-20 per group, *ANOVAD all groups vs. C57BL/6J TPCs inj. into C57BL/6J mice p<0.0001).

FIG. 14 is a histogram showing the results of mouse IL-6 ELISA of supernatants from C57BL/6J resting peritoneal macrophages incubated with lipid free APOA-I (5 µg/mL: 8 h), APOE3 (5 µg/mL; 8, 24 h) and heat-denatured APOE3 (dAPOE3, 5 µg/mL; 24 h) with or without LPS (25 ng/mL) (n=4 per group, MWt: *8 h APOA-I/LPS and APOE/LPS vs. LPS p=0.0284; †8 h APOA-I and APOE vs. CTL p=0.0284; #24 h APOE vs. CTL p=0.05; ‡24 h dAPOE3 vs. APOE3 group p=0.0022).

FIG. 15 is a histogram showing the levels of IL-6 mRNA measured by quantitative RT-PCR and normalized with S26 mRNA of C57BL/6J and $Cx3cr1^{GFP/GFP}$, and $Cx3cr1^{GFP/GFP}ApoE^{-/-}$ PEM cultured for 24 h with CXCL1 (n=5 per group, MWt: *C57BL/6J vs. $Cx3cr1^{GFP/GFP}$ p=0.0159; ‡ $Cx3cr1^{GFP/GFP}$ vs. $Cx3cr1^{GFP/GFP}ApoE^{-/-}$ p=0.0079).

FIG. 16 is a histogram showing the levels of mouse IL-6 ELISA levels of supernatants of C57BL/6J and $Cx3cr1^{GFP/GFP}$, and $Cx3cr1^{GFP/GFP}ApoE^{-/-}$ PEM cultured for 24 h with CXCL1 (n=5 per group, MWt: *C57 vs. $Cx3cr1^{GFP/GFP}$ p=0.0159; ‡$Cx3cr1^{GFP/GFP}$ vs. $Cx3cr1^{GFP/GFP}$ $ApoE^{-/-}$ p=0.0079).

FIG. 39 is a histogram showing the results of the quantification of Mouse IL-6 ELISA of supernatants from C57BL/6J peritoneal Mφs incubated for 24 h in control medium, lipid free APOE3 (5 μg/mL), APOE3 (5 μg/mL) and Polymyxin B (25 μg/mL), heat-denatured APOE3 (dAPOE3, 5 μg/mL), APOE3 (5 μg/mL) and rat IgG1 isotype control (IgG1, 100 μg/mL) or APOE3 (5 μg/mL) and rat anti-CD14 antibody (aCD14 Ab, 100 μg/mL) (n=5-6/group; One way ANOVA/Bonferroni multi-comparison tests; *APOE3 vs. CTL p<0.0001; # dAPOE3 vs. APOE p<0.0001; APOE3 IgG vs. CTL p<0.0001; APOE3 IgG vs. APOE3 aCD14 Ab p<0.0001, Mann & Whitney t tests; *APOE3 vs. CTL p=0.0043; # dAPOE3 vs. APOE3 p=0.0117; APOE3 IgG vs. CTL p=0.0080; APOE3IgG vs. APOE3 aCD14 Ab p=0.0117. The experiment was repeated twice with similar results.

FIG. 40 is a histogram showing the results of the quantification of subretinal IBA-1+MPs/impact localized on the lesion surrounding RPE of Cx3cr1$^{GFP/GFP}$ mice treated with control IgG, IL-6- or CD14-blocking antibodies (calculated intraocular concentration 5 μg/ml; n=13-14/group. One way ANOVA/Dunnett's post-hoc tests of IgG vs. any other group *p<0.001, Mann & Whitney test *IgG vs anti IL-6 p=0.0021; IgG vs anti CD14 p=0.0028).

FIG. 41 is a histogram showing the results of the quantification of CD102+ CNV area on RPE/choroidal flatmounts of C57BL/6J (n=8 eyes), Cx3cr1$^{GFP/GFP}$ (n=8), Cx3cr1$^{GFP/GFP}$ApoE$^{-/-}$ (n=10) and ApoE$^{-/-}$ (n=10) mice, 7 days after laser injury (n=8-10/group; One way ANOVA/Bonferroni Cx3cr1$^{GFP/GFP}$ vs. Cx3cr1$^{GFP/GFP}$ ApoE$^{-/-}$ *p<0.0001. Independent Mann & Whitney t-tests of Cx3cr1$^{GFP/GFP}$ vs. Cx3cr1$^{GFP/GFP}$ApoE$^{-/-}$; p<0.0001). Scale bars=50 μm. The quantification of CD102 staining confirms the exaggerated CNV in Cx3cr1$^{GFP/GFP}$-mice and shows that CNVs are significantly smaller in Cx3cr1$^{GFP/GFP}$ApoE$^{-/-}$-mice.

FIG. 42 is a histogram showing the results of the quantification of CD102+CNV area on RPE/choroidal flatmounts of Cx3cr1$^{GFP/GFP}$-mice treated with control IgG, IL-6 or CD14-blocking antibodies (calculated intraocular concentration 5 μg/mL; n=8-10 eyes/group. One way ANOVA/Dunnett's post-hoc tests of IgG vs. any other group *p=0.0197. Mann & Whitney t test *IgG vs. anti IL-6 p<0.0001; IgG vs. antiCD14 p=0.015) Scale bars=50 μm. Quantification of the CD102 staining shows that the CNV in Cx3cr1$^{GFP/GFP}$-mice treated with CD14-, and IL-6-blocking antibodies are significantly smaller when compared to CNV in control IgG treated Cx3cr1$^{GFP/GFP}$-mice.

FIG. 43 is a histogram showing the results of the quantification of traceable nucleotide EdU+ nuclei after 1 day of cell culture. The proliferation rates of WT- and Cx3cr1$^{GFP/GFP}$-Macrophages are low and not significantly different from each other. APOE3 or IL-6 do not increase the proliferation rate. Neither APOE3 nor IL-6 increase the proliferation rate.

EXAMPLES

Figure 1:
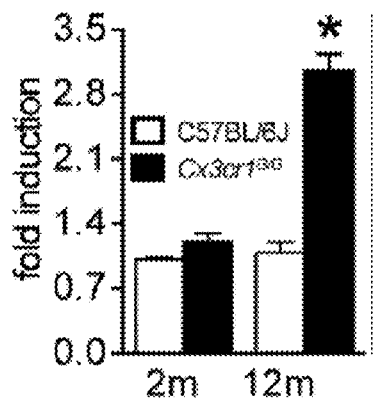
FIG. 1 is a histogram showing the levels of ApoE mRNA measured by quantitative RT-PCR and normalized with β-actin mRNA in 2 months- and 12 months-old C57BL/6 and Cx3cr1$^{GFP/GFP}$ mouse eyes (n=6 per group, *Mann-Whitney U test (MWt) 12 months p=0.0043).

The present invention is further illustrated by the following examples.

Materials and Methods

Animals

Cx3cr1$^{GFP/GFP}$, ApoE$^{-/-}$, Fas$^{lpr}$, FasL$^{gld}$, APOε2, APOε3 and APOε4-TR mice were purchased (Charles River Laboratories, Jackson laboratories, Taconic) and Cx3cr1$^{GFP/GFP}$ApoE$^{-/-}$ mice were generated (Combadiere et al., 2003). Mice contaminated with the Crb1rd8 mutation were backcrossed to C57BL/6J mice to eliminate the mutation. All mice were thus negative for the Crb1$^{rd8}$, Pde6b$^{rd1}$ and Gnat2$^{cpfl3}$ mutations. Mice were housed in the animal facility under specific pathogen-free condition, in a 12/12 h light/dark (100-500 lux) cycle with water and normal diet food available ad libitum. All animal experiments were approved by the local Animal Care ethics Committee "Comité d'éthique en experimentation animale Charles Darwin" (No. p3/2008/54).

APOE, IBA-1, CD18 Immunohistochemistry on Donor Samples.

Donor eyes with a known history of AMD and controls were collected through the Minnesota Lions Eye bank. Postmortem fundus photographs were taken and the posterior segment was fixed 4 h in 4% PFA, transported in PBS, dissected, imbedded in paraffin, and sectioned (5 control maculae; 5 GA donor maculae). Donors gave informed consent in accordance with the eye bank's ethics committee, 5 tonsillectomy surgical samples, removed for recurrent acute tonsillitis, were recuperated from tonsillectomies at the Fondation Rothschild and then fixed and sectioned in the same way. For flatmount immunohistochemistry, donor eyes with visible atrophic areas (5 eyes), visible large drusen on RPE flatmounts (5 eyes), and controls (3 eyes) were dissected into approximately 5×5 mm tissue parts and immunohistochemistry was performed on submerged samples. APOE (M068-3 mouse-anti-human, citrate buffer heat antigen retrieval for paraffin sections, MBL), IBA-1 (rabbit-anti-human, formic acid antigen retrieval, Wako Chemicals), and CD18 (MCA503, rat-anti-human, citrate buffer heat antigen retrieval, Abd Serotec) immunohistochemistal analyses were performed and revealed using appropriate fluorescent or alkaline-phosphatase coupled secondary antibodies (Molecular Probe) using a Fast Red substrate kit (Sigma).

Immunohistochemistry, Mononuclear Phagocyte Quantification, and Histology

Human and murine Retinal pigment epithelium (RPE) and retinal flatmounts and human and murine sections were stained and quantified as previously described (Sennlaub et al., 2013) using polyclonal goat anti human APOE (Millipore), polyclonal rabbit anti-IBA-1 (Wako), polyclonal rabbit anti-rat FASL (Millipore), monoclonal rat anti-mouse IL-6 (R&D Systems), AlexaFluor 555 phalloidin (Mol probes), and rat anti-mouse CD102 (clone 3C4. BD Biosciences Pharmingen) appropriate secondary antibodies and counterstained with Hoechst if indicated. Preparations were observed with fluorescence microscope (DM5500, Leica) or a FV 1000 (Olympus) confocal microscope.

Histology of mice eyes and photoreceptor quantification were performed as previously described (Sennlaub et al., 2013).

Cell Preparations and Cell Culture

Resident and thioglycolate-elicited peritoneal cell, peritoneal macrophages, BMM (bone marrow-derived monocytes), brain microglial cell, and POS (Photoreceptor segment) isolation, as BMM, TPM (thioglycolate-elicited peritoneal macrophages), RPM (Resident peritoneal macrophages), and MP- and BMM-retinal explant co-cultures (all in serum-free X-Vivo 15 medium) were performed as previously described (Sennlaub et al., 2013). In specific experiments, cells were stimulated by recombinant human CX3CL1, APOA-1, APOE2, APOE3 or APOE4 (Leinco Technologies), APOE (5 µg/ml, Leinco Technologies), APOE (5 µg/ml) with Polymyxin B (25 µg/ml, Calbiochem), heat-denatured APOE (5 µg/ml, 95° C., 90 min,), rat anti-IgG isotype control (100 µg/ml, R&D), rat anti-mouse CD14 (100 µg/ml, R&D), rat anti-mouse TLR2 (100 µg/ml, R&D) and POS prepared as previously described (Molday et al, 1987). For in vitro apoptosis experiments, 100 000 Mos or Mφs of the different genotypes were cultured for 24 h with or without MegaFasL (AdipoGen). TUNEL staining (In Situ Cell Death Detection Kit, Roche Diagnostics) was performed according to the manufacturer's instructions; TUNEL$^+$ and Hoechst$^+$ nuclei were counted automatically using the Array Scan (Thermofischer).

Subretinal Mononuclear Phagocyte Cell Clearance

RPCs (resident peritoneal cells). TPCs (thioglycolate-elicited peritoneal cells, containing 70% Mφs). BMMs (bone marrow-derived monocytes, ~95% pure) and Microglial cells (~95% pure) were labeled in 10 µM CFSE (Life technologies). Cells were washed and resuspended in PBS. 12000 cells (4 µl) were injected in the subretinal space of anesthetized 2 months-old mice using a microinjector and glass microcapillaries (Eppendorf). A hole was pierced with the glass capillary prior to the subretinal injection to avoid intra-ocular pressure increase and to allow retinal detachment with 4 µl of solution. The subretinal injection was verified by fundoscopy. In specific experiments, Mφs, RPCs and TPCs were co-injected with rhApoE3 (Leinco Technologies), rmIL-6, rat anti-mouse IL-6, rat anti-mouse CD14 the isotype control rat IgG1 (R&D Systems), or MegaFasL (AdipoGen). Intraocular concentrations were calculated as a dilution of 10× of the injected solution, as the injected 4 µl correspond to approximately $\frac{1}{10}^{th}$ of the intraocular volume. Eyes were enucleated after 24 hours, fixed in 4% PFA, and flatmounted. The flatmounts were double labelled with anti-F4/80 antibody to identify CSFE+F4/80 Mφs and counted on the subretinal aspect of the retinal flatmount and the RPE/choroid flatmount of each eye). Eyes with subretinal hemorrhages were discarded. Double-labeled mononuclear phagocytes in subretinal space were quantified on Retinal pigment epithelium flatmounts and the subretinal side of retinal flatmounts.

Flow Cytometry

Cytometry was performed as previously described (Camelo et al., 2012), using anti-CD11b PE, anti F4/80 Pacific Blue or APC, PI, Annexin V-biotin, streptavidin APC (all from Abd Serotec). Acquisition was performed on LSRII cytometer (BD Biosciences) and data were analyzed with FlowJo 7.9.

Western Blot, Reverse Transcription and Real-time Polymerase Chain Reaction and ELISA WB analysis was performed using a polyclonal goat anti-ApoE (millipore) as previously described (Houssier et al., 2008). RT-PCRs using Sybr Green (Life Technologies) and ELISAs using human APOE ELISA kit (Mabtech) and mouse IL-6 DuoSet (R&D Systems) were performed as previously described (Sennlaub et al., 2013).

Statistical Analysis

Graph Pad Prism 5 and 6 (GraphPad Software) were used for data analysis and graphic representation. All values are reported as mean±SEM. Statistical analysis was performed by one-way Anova analysis of variance followed by Bonferroni or Dunnett's post-test (multiple comparison) or Mann-Whitney U test (2-groups experiments) for comparison among means depending on the experimental design. The n and p-values are indicated in the figure legends. For experiences comprising subretinal MP injections, a pilot study revealed that severe hemorrhage secondary to subretinal injection interferes with MP clearance and was used as exclusion criteria.

Terminal Deoxynucleotidyl Transferase dUTP Nick End Labeling (TUNEL) on Flatmounts 4% PFA fixed retinal flatmounts were post-fixed in frozen methanol/acetic acid (2:1) for 30 min and washed in PBS. Flatmounts were incubated overnight at 4° C. with the terminal transferase and the supplied buffer (In Situ Cell Death Detection Kit, Roche Diagnostics). Flatmounts were then incubated at 37° C. for 90 min and the reaction was stopped by washing with PBS. Nuclei were counterstained with Hoechst (Sigma-Aldrich), Flatmounts images were captured with a DM5500 microscope (Leica).

Light-challenge and Laser-injury Model

Two- to four-month-old mice were adapted to darkness for 6 hours, pupils dilated and exposed to green LED light (starting at 2 AM, 4500 Lux, JP Vezon equipments) for 4 days as previously described (Sennlaub et al, 2013). Laser-coagulations were performed with a 532 nm ophthalmological laser mounted on an operating microscope (Vitra Laser, 532 nm, 450 mW, 50 ms and 250 µm). Intravitreal injections of 2 µl of PBS, isotype control rat IgG1, rat anti-mouse IL-6 (R&D Systems), and rat anti-mouse CD14 (BD Biosciences) were performed using glass capillaries (Eppendorf) and a microinjector. The 2 µl solution of the antibodies were injected at 50 µg/ml, corresponding to an intraocular concentration of 5 µg/ml assuming their dilution by approximately $1/10^{th}$ in the intra-ocular volume.

Example 1

Subretinal Mononuclear Phagocytes (MPs) Cluster in and Around Soft Drusen in Early AMD and Express ApoE Physiologically, the subretinal space does not contain significant numbers of MPs, possibly due in part to immunosuppressive RPE signals (Streilein et al. 2002).

Mononuclear phagocytes are nevertheless known to be present in the subretinal space and on the apical side of Retinal pigment epithelium cells adjacent to the lesions of atrophic AMD.

Experiments conducted on Retinal pigment epithelium/choroidal flatmounts of soft drusen from donors with intermediate AMD demonstrate that numerous CD18+ and IBA-$1^+$ cells are contained within soft drusen (partially covered by the Retinal pigment epithelium), but also adjacent to the soft drusen on the surrounding autofluorescent Retinal pigment epithelium (data not shown). Higher magnification with lateral Z stack projections through a subretinal IBA-1+ mononuclear phagocyte further demonstrates the close physical contact of the mononuclear phagocytes with the autofluorescent Retinal pigment epithelium (data not shown). Subretinal mononuclear phagocytes in contact with the Retinal pigment epithelium are observed in the vicinity of all soft drusen examined (5 eyes). Subretinal mononuclear phagocytes are very rare at distance from soft drusen, and in healthy maculae (3 eyes). APOE and IBA-1 double labeling on the subretinal side of the overlaying retina (to avoid masking by Retinal pigment epithelium autofluorescence) shows that subretinal IBA-$1^+$ mononuclear phagocytes strongly express APOE when compared to the vitreal aspect of the inner retina in which APOE is observed in IBA-$1^+$ highly ramified microglial cells.

Taken together, these results demonstrate that subretinal mononuclear phagocytes are present in early AMD, where they cluster in and around soft drusen. They are in close contact with the Retinal pigment epithelium and strongly express APOE in a manner similar to macrophages in the inflammation of other tissues, such as atherosclerotic lesions.

Example 2

Subretinal Mononuclear Phagocytes (MPs) Accumulate on the RPE in the Vicinity of Atrophic Lesions and Large Drusen In late AMD, immunohistochemical studies on sections have revealed the presence of subretinal MPs on RPE cells adjacent to the lesions of atrophic AMD (Gupta et al, 2003; Sennlaub et al, 2013) and MPs were found in subretinal neovascular membranes (Oh et al. 1999). Because the small, dispersed MPs are difficult to detect on sections, MP-marker-IBA-1 immunohistochemistry was thus performed on healthy and diseased macular RPE/choroidal flatmounts (IBA-1 green fluorescence, RPE autofluorescence visible as orange due to its autofluorescence in the red and green channel). Confocal microscopy confirmed that subretinal IBA-$1^+$MPs are only very occasionally observed in healthy age-matched donor central RPE (data not shown). Within the atrophic lesions of GA patients where the RPE has disappeared, MPs were numerous, but were also invariably observed on the apical side of the RPE adjacent to the lesions. Furthermore, large drusen (>125 µm), visible under the dissecting microscope as pale lesions after removal of the retina and as dome-shaped protrusions under the confocal microscope, were shown to contain numerous IBA-$1^+$ cells within the drusen, but also on the adjacent RPE (data not shown). Double-labeling on the subretinal side of the overlaying retina (to avoid masking by RPE autofluorescence) showed that subretinal IBA-$1^+$MPs also express the pan-MP marker CD18. IBA-$1^+$MPs in close contact with the RPE were observed in the vicinity of all examined large drusen and atrophic zones.

These observations considered together confirm the presence of subretinal MPs in AMD (Gupta et al, 2003; Penfold et al, 1985; Sennlaub et al, 2013) and illustrate their accumulation around large drusen and GA lesions in contact with the RPE. They are very rare in healthy donors. This further suggests that RPE-mediated immunosuppression is impaired in intermediate AMD (large drusen) and late AMD (GA).

Example 3

Subretinal MPs Accumulated on the RPE in the Vicinity of Atrophic Lesions and Large Drusen Express APOE MPs have been reported to express APOE at high levels (Basu et al, 1982; Nakai et al, 1996; Peri & Nusslein-Volhard, 2008; Rosenfeld et al, 1993). Immunohistochemistry of APOE and IBA-1 on paraffin sections of human tonsils, which were used as a positive control, confirmed that IBA-$1^+$MPs can strongly express APOE (data not shown). Similarly, on retinal flatmounts of donor eyes with large drusen. APOE staining was observed in and around subretinal IBA-$1^+$MPs (data not shown). The double labeling was performed on the subretinal side of retinas to avoid masking by the RPE autofluorescence. APOE staining was performed on paraffin sections of controls and donor eyes with geographic atrophy lesions. A substrate revealing method (alkaline phosphatase/Fast Red) that is visible in bright field was used to circumvent confusion with RPE autofluorescence. In sections from control eyes the APOE signal was concentrated at the basal portion of the RPE (data not shown). In donor eyes with GA, adjacent to the atrophic area, a strong APOE signal was observed in the RPE, but it was less restricted to the basal aspect than in controls. Additionally, APOE immunostaining was observed in cells adjacent to the RPE. Double labeling with IBA-1 identified these cells as subretinal IBA-$1^+$MPs. Omitting the APOE-antibody and following the same experimental protocol did not produce any significant staining.

Taken together, these results show that, in addition to the RPE, subretinal MPs in AMD patients strongly express APOE in a manner similar to other inflammatory settings (eg: atherosclerotic lesions (Rosenfeld et al. 1993)).

Example 4

APOE Promotes Subretinal MP Accumulation and Photoreceptor Degeneration in Cx3Cr1$^{GFP/GFP}$ Mice It is known that, in the eye, CX3CL1 is constitutively expressed as a transmembrane protein in inner retinal neurons (Silverman et al., 2003; Zieger et al., 2014) and the Retinal pigment epithelium, providing a tonic inhibitory signal to CX3CR1-bearing retinal microglial cells (MCs) that keep these cells in a quiescent surveillance mode under physiological conditions (Combadiere et al., 2007; Ransohoff, 2009). Deletion or deficiency of Cx3cr1 in mice leads to a strong increase of subretinal mononuclear phagocyte accumulation with age, after light-challenge or laser-injury (Combadiere et al, 2007; Ma et al, 2009; Raoul et al, 2008), in diabetes (Kezic et al, 2013), and in a paraquat-induced retinopathy model (Chen et al, 2013). Cx3cr1$^{GFP/GFP}$ mice do not develop drusen and Retinal pigment epithelium atrophy, but display subretinal mononuclear phagocyte accumulation on the RPE similar to AMD, as well as the associated photoreceptor degeneration and excessive CNV observed in AMD (Combadiere et al., 2007, Sennlaub et al., 2013). Cx3cr1$^{GFP/GFP}$ mice may thus help decipher AMD's underlying mechanism. The APOE localization in 12-month-old Cx3cr1$^{GFP/GFP}$-mice presenting subretinal MP accumulation was evaluated (Sennlaub et al. 2013).

Immunohistochemical localization of APOE on retinal sections and the subretinal side of retinal flatmounts of both 12 months-old wildtype- and Cx3cr1$^{GFP/GFP}$ mice reveals APOE localization mainly in the RPE and inner retina as previously described (Anderson et al, 2001) (data not shown). Additionally, a strong signal was detected in cells apposed to the RPE on retinal sections and the subretinal side of retinal flatmounts in aged Cx3cr1$^{GFP/GFP}$-mice, that were identified as IBA-1 expressing MPs, similar to AMD patients. Further, ApoE mRNA is significantly increased in 12 months-old eyes of Cx3cr1$^{GFP/GFP}$ (FIG. 1) mice, when subretinal mononuclear phagocyte accumulation occurs (Sennlaub et al., 2013).

Figure 2:
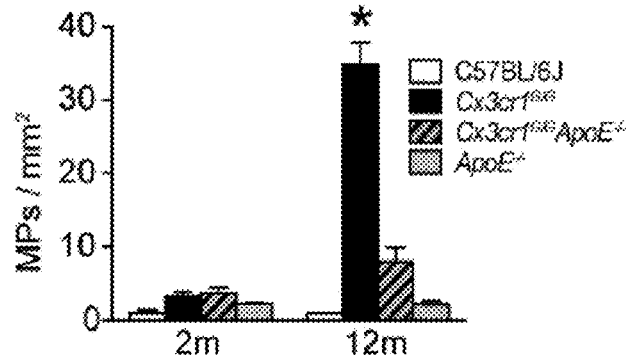
FIG. 2 is a histogram showing the results of quantification of subretinal IBA-1+ mononuclear phagocytes (MPs) in 2 months- and 12 months-old C57BL/6J, Cx3cr1$^{GFP/GFP}$, Cx3cr1$^{GFP/GFP}$ApoE$^{-/-}$, and ApoE$^{-/-}$ mice (n=10-22 per group, *one-way ANOVA Bonnferoni's multiple comparison test (ANOVAB) Cx3cr1$^{GFP/GFP}$ vs any other group at 12 months p<0.0001).

To evaluate the role of APOE in subretinal mononuclear phagocyte (MP) accumulation, Cx3cr1$^{GFP/GFP}$ ApoE$^{-/-}$ mice were analyzed. Quantification of subretinal IBA-1$^+$ mononuclear phagocytes on retinal and Retinal pigment epithelium/choroidal flatmounts of 12 months-old Cx3cr1$^{GFP/GFP}$ and Cx3cr1$^{GFP/GFP}$ApoE$^{-/-}$ mice showed that the significant age-dependent subretinal mononuclear phagocyte accumulation observed in Cx3cr1$^{GFP/GFP}$ mice (compared to C57BL/6J and ApoE$^{-/-}$ mice) was nearly completely inhibited in Cx3cr1$^{GFP/GFP}$ApoE$^{-/-}$ mice (FIG. 2). These results show that APOE is essential for age-dependent subretinal mononuclear phagocyte accumulation in Cx3cr1$^{GFP/GFP}$ mice.

Figure 3:
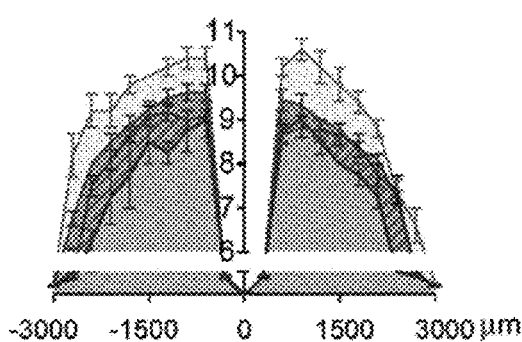
FIG. 3 is a graph showing the photoreceptor nucleus rows at increasing distances (−3000 μm; inferior pole, +30001 μm; superior pole) from the optic nerve (0 μm) in 12 months-old C57BL/6J, Cx3cr1$^{GFP/GFP}$, Cx3cr1$^{GFP/GFP}$ApoE$^{-/-}$, and ApoE$^{-/-}$ mice.

Next, the outer nuclear layer (ONL) containing the photoreceptor nuclei on histological sections of 12 months-old C57BL/6J, ApoE$^{-/-}$, Cx3cr1$^{GFP/GFP}$, and Cx3cr1$^{GFP/GFP}$ApoE$^{-/-}$ mice was examined to evaluate the influence of APOE deficiency on photoreceptor degeneration. At equal distance from the optic nerve, ApoE$^{-/-}$ mice present a thinned but regular outer nuclear layer, attributed to the lack of systemic APOE and disturbed systemic lipid transport and retinal cholesterol trafficking, as previously described (Ong et al., 2001). Interestingly, the outer nuclear layer of Cx3cr1$^{GFP/GFP}$ApoE$^{-/-}$ mice is similar to ApoE$^{-/-}$ mice and thicker and more regular than in Cx3cr1$^{GFP/GFP}$ mice, in which inflammation-associated photoreceptor degeneration occurs similar to that observed in Cx3cr1$^{-/-}$ mice (Sennlaub et al., 2013). Photoreceptor nuclei row counts at increasing distances from the optic nerve (0 μm) (FIG. 3) and calculation of the area under the curve (FIG. 4) showed that Cx3cr1$^{GFP/GFP}$ApoE$^{-/-}$ mice are significantly protected against age-dependent photoreceptor cell loss when compared to Cx3cr1$^{GFP/GFP}$ mice and not significantly different to ApoE$^{-/-}$ mice.

Figure 4:
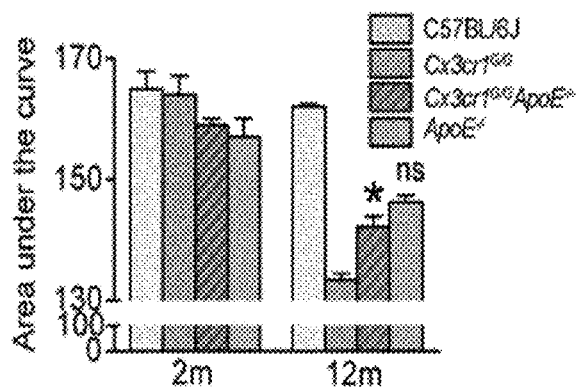
FIG. 4 is a histogram showing the quantification of the area under the curve of photoreceptor nucleus row counts of 2 and 12 months-old C57BL/6J. Cx3cr1$^{GFP/GFP}$, Cx3cr1$^{GFP/GFP}$ApoE$^{-/-}$, and ApoE$^{-/-}$ mice (n=7-12, *MWt Cx3cr1$^{GFP/GFP}$ vs Cx3cr1$^{GFP/GFP}$ApoE$^{-/-}$ p=0.026: *ANOVAB Cx3cr1$^{GFP/GFP}$ vs Cx3cr1$^{GFP/GFP}$ApoE$^{-/-}$ at 12 months p<0.0001).

In summary, the above experiments demonstrate that ApoE deletion significantly inhibited the age-dependent photoreceptor degeneration (FIGS. 3 and 4) and exaggerated CNV observed in Cx3cr1$^{GFP/GFP}$-mice (FIG. 4I). APOE expression is thus increased and necessary for age-dependent accumulation and inflammation-associated photoreceptor degeneration in Cx3cr1-deficient mice.

Figure 32:
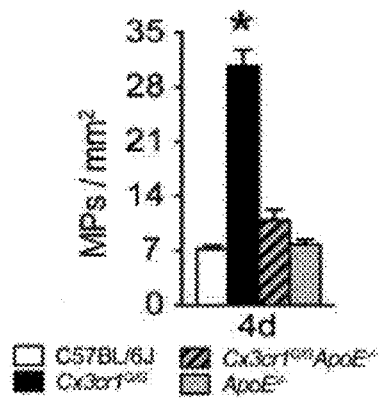
FIG. 32 is a histogram showing the results of the quantification of subretinal IBA-1+MPs in 2 m-(left) and 12 m-(right) old mice of the indicated strains C57BL/6J (WT), $Cx3cr1^{GFP/GFP}$, $Cx3cr1^{GFP/GFP}ApoE^{-/-}$ and $ApoE^{-/-}$ (n=10-25/group ANOVA/Dunnett test; $Cx3cr1^{GFP/GFP}$ vs. any other group *p<0.0001; Mann & Whitney t test of $Cx3cr1^{GFP/GFP}$ vs. $Cx3cr1^{GFP/GFP}ApoE^{-/-}$ *p<0.0001).

Similarly. Cx3cr1$^{GFP/GFP}$ApoE$^{-/-}$-mice were found to be significantly protected against the subretinal MP accumulation observed in Cx3cr1$^{GFP/GFP}$-mice after four days of light-challenge (FIG. 32). It should be noted that the intensity of the light-challenge model used herein was sufficient to induce subretinal inflammation in the Cx3cr1$^{-/-}$ mice but did not cause significant subretinal inflammation nor degeneration in WT mice (Sennlaub et al, 2013). Moreover, seven days after a laser-impact, subretinal IBA-1$^+$MPs counted on the RPE at a distance of 0-500 μm to CD102$^+$CNV in Cx3cr1$^{GFP/GFP}$ and Cx3cr1$^{GFP/GFP}$ApoE$^{-/-}$-mice were significantly inhibited in Cx3cr1$^{GFP/GFP}$ApoE$^{-/-}$-mice (data not shown).

C57BL/6J (WT) mice are inbred and carry Pde6b$^{rd1}$ (retinal degeneration 1), Crb1$^{rd8}$ (retinal degeneration 8), Gnat2$^{cpfl3}$ (Cone photoreceptor function loss3) mutations relatively commonly (Chang et al. 2013). These mutations can lead to subretinal inflammation secondary to primary retinal degeneration (Luhmann et al, 2012). In the experiments performed, all mice strains used tested negative for these three mutations. Furthermore, subretinal MP accumulation in 12 m-old Cx3cr1$^{+/GFP}$, and Cx3cr1$^{GFP/GFP}$ littermates of Cx3cr1$^{+/GFP}$ breeders showed no evidence of influence from an unknown contributor gene specific to the Cx3cr1$^{GFP/GFP}$mouse line (data not shown). Cx3cr1$^{GFP/GFP}$ApoE$^{-/-}$-mice were generated twice with independently purchased Cx3cr1$^{GFP/GFP}$ and ApoE$^{-/-}$-mice (once at the Laboratoire Immunité et Infection and once at the Institut de la Vision) and both Cx3cr1$^{GFP/GFP}$ ApoE$^{-/-}$-mice strains generations were protected against the subretinal MP accumulation observed in the two Cx3cr1$^{GFP/GFP}$- mice strains of the two sites. Taken together, these results make it highly unlikely that the MP accumulation in Cx3cr1$^{GFP/GFP}$ mice and the protection in Cx3cr1$^{GFP/GFP}$ApoE$^{-/-}$-mice are due to genes other than Cx3cr1 and ApoE.

In summary, the above experiments demonstrate that APOE is robustly expressed in subretinal MPs, more strongly expressed in Cx3cr1$^{GFP/GFP}$ MPs, and that ApoE deletion very significantly inhibited the age-, light-, and laser-induced accumulation of subretinal MPs observed in Cx3cr1-deficient mice.

Example 5

Figure 5:
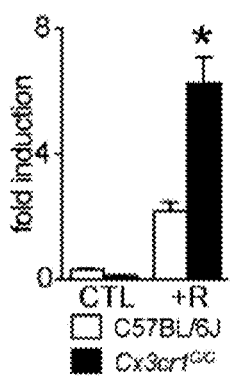
FIG. 5 is a histogram showing the levels of ApoE mRNA measured by quantitative RT-PCR and normalized with S26 mRNA of C57BL/6J and Cx3cr1$^{GFP/GFP}$ BMM cultured for 24 h in control conditions and in contact with POS of an overlaying retinal explant (n=4 per group, *MWt between+ retinal explant (+R) groups p=0.0286).
Figure 6:
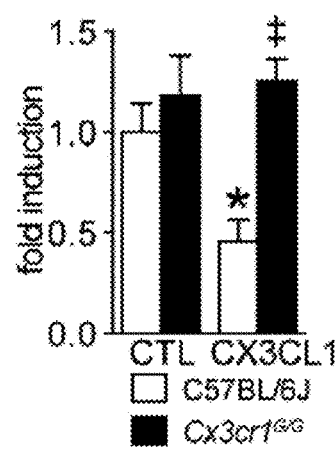
FIG. 6 is a histogram showing the levels of ApoE mRNA measured by quantitative RT-PCR and normalized with S26 mRNA of C57BL/6J and Cx3cr1$^{GFP/GFP}$ PEM cultured for 24 h in control conditions and with CX3CL1 (n=4 per group, *MWt WT with and without CX3CL1 p=0.0286; ‡ MWt CX3CL1 groups p=0.028).

ApoE, Controlled by CX3CR1, Regulates Subretinal Mononuclear Phagocyte Clearance In Cx3cr1$^{GFP/GFP}$ mice, subretinal mononuclear phagocytes, are in part derived from monocytes (Mos) and microglial cells (Mcs) (Sennlaub et al., 2013) and all express Cx3cr1 promotor-controlled GFP. To test whether CX3CL1/CX3CR1 signaling directly controls APOE expression in mononuclear phagocytes and to evaluate whether Cx3cr1$^{GFP/GFP}$ MPs differ in their ApoE expression, C57BL/6J (WT) and Cx3cr1$^{GFP/GFP}$-Mo (prepared from bone marrow) cultured for 24 h in contact with the photoreceptor segment (POS) of an overlaying retinal explant (expressing CX3CL1) were studied, by simulating the conditions of mononuclear phagocyte differentiation in the subretinal space. RT-PCRs showed that ApoE mRNA is induced at a significantly higher rate in Cx3cr1$^{GFP/GFP}$-Mo- in the presence of POS of an overlaying retinal explant (FIG. 5). Accordingly. ApoE mRNA transcription of WT thioglycolate-elicited peritoneal Macrophages (TPMs) expressing APOE and CX3CR1 is inhibited by CX3CL1, and significantly lower when compared to Cx3cr1$^{GFP/GFP}$ TPMs (FIG. 6).

Figure 7:
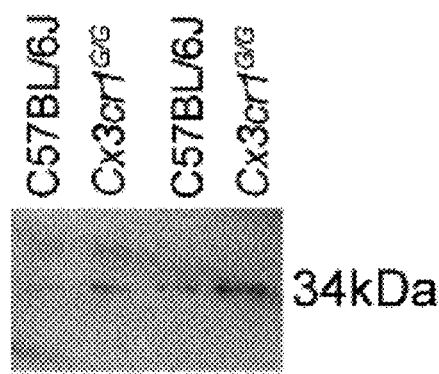
FIG. 7 is a photograph showing the result of a western blot analysis of equivalent amounts of supernatant protein from CX3CL1-exposed C57BL/6J and Cx3cr1$^{GFP/GFP}$ PEM at 24 h.
Figure 8:
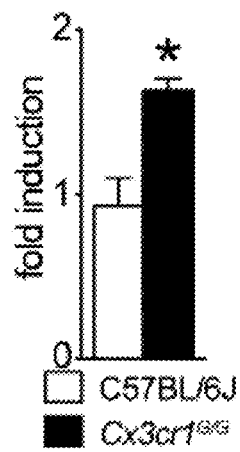
FIG. 8 is a histogram showing the levels of ApoE mRNA measured by quantitative RT-PCR and normalized with S26 mRNA of C57BL/6J and Cx3cr1$^{GFP/GFP}$ FACS-sorted microglial cells (MCs), freshly extracted from adult brain.

Western blot analysis of equivalent amounts of supernatant protein from CX3CL1-exposed TPMs also show increased APOE secretion (FIG. 7) in the Cx3cr1$^{GFP/GFP}$ samples (Western blots are used, as mouse APOE ELISA kits, tested on ApoE$^{-/-}$ serum, proved unreliable), when compared to the soluble Mer receptor tyrosine kinase that is released constitutively from cultured macrophages (Sather et al., 2007) and which served as a loading control (data not shown). Significantly increased amounts of ApoE mRNA are also observed in FACS-sorted microglial cells freshly extracted from adult Cx3cr1$^{GFP/GFP}$ brain when compared to the control (FIG. 8).

The reasons for which subretinal MPs accumulate in Cx3cr1$^{GFP/GFP}$ mice are not fully understood. Theoretically, the numbers of subretinal MPs is determined by i) recruitment, ii) in situ proliferation, iii) migration (egress), and/or iv) apoptotic clearance. The accumulation of MPs in Cx3cr1-deficient mice was shown to result from the overexpression of CCL2 by Cx3cr1$^{GFP/GFP}$ MPs, which in turn leads to increased CCR2$^+$Mos recruitment from the blood (Sennlaub et al, 2013). Local injections of the traceable nucleotide EdU in light-challenged Cx3cr1$^{GFP/GFP}$-mice failed to be incorporated in subretinal MPs, suggesting that in situ proliferation does not significantly contribute to the accumulation (supplementary material of Sennlaub et al. 2013). To evaluate whether subretinal MPs egress from the subretinal space or undergo apoptosis, 12,000 CFSE-stained WT- and Cx3cr1$^{GFP/GFP}$-thioglycollate-elicited peritoneal cells (containing 70% Mϕs) were adoptively transferred in the subretinal space of WT mice and the number of F4/80 expressing Mϕs that co-stained for CFSE on RPE- and retinal-flatmounts once retinal detachment had subsided (8-12 h) was counted.

Figure 9:
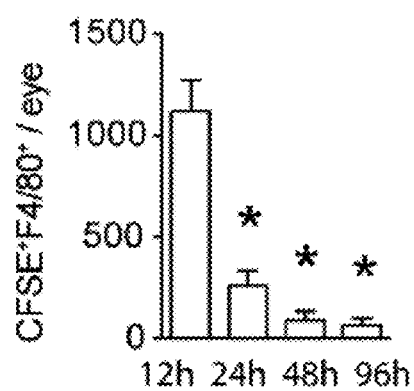
FIG. 9 is a histogram showing the quantifications of CFSE$^+$F4/80$^+$ macrophages at different time points after subretinal injections of CFSE$^+$ TPCs (n=6, *one-way ANOVA Dunnett's multiple comparison test (ANOVAD) each group vs 12 h group p<0.0001).
Figure 10:
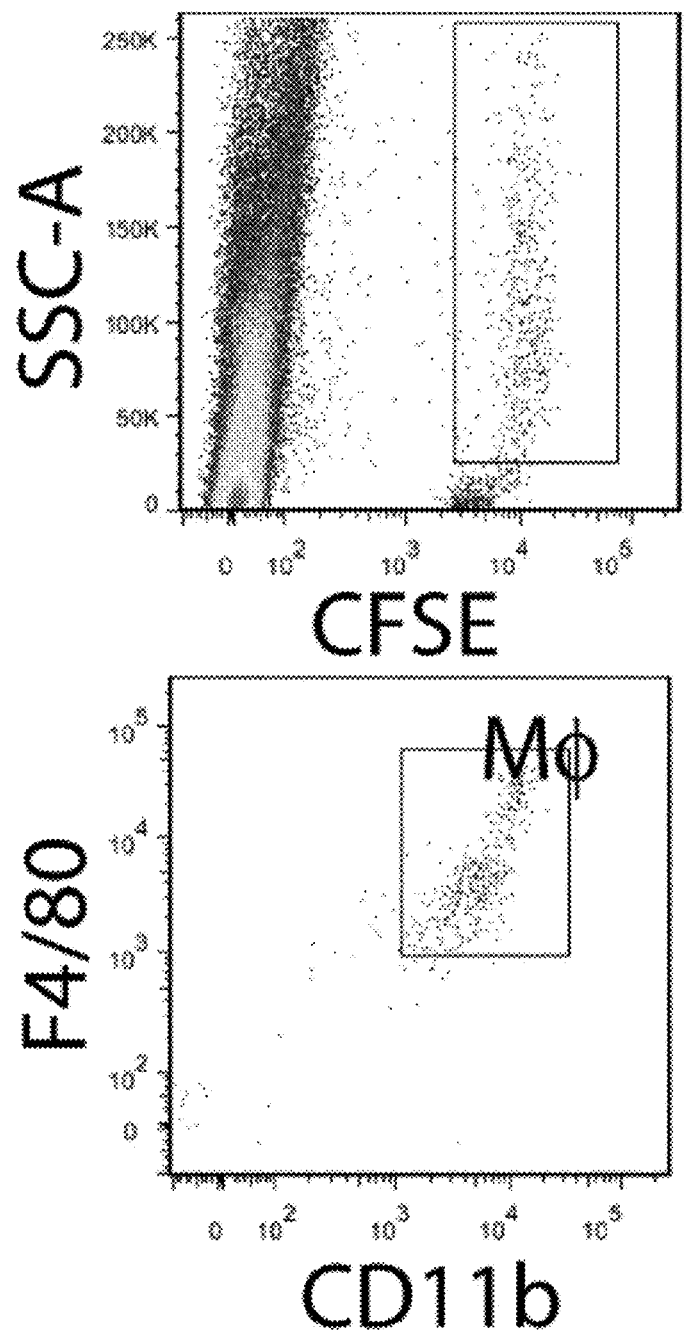
FIG. 10 is a photograph showing representative cytometry images of SSC-A/CFSE and CD11b/F4/80 gated analysis of eye cell suspensions prepared 24 h after the injection of Cx3cr1$^{GFP/GFP}$ CFSE$^+$TPCs and cytometric quantification of eye cell suspensions at 24 h after the injection of C57BL/6J and Cx3cr1$^{GFP/GFP}$ TPCs into C57BL/6J (n=16-20 per group, *MWt p=0.0024).
Figure 33:
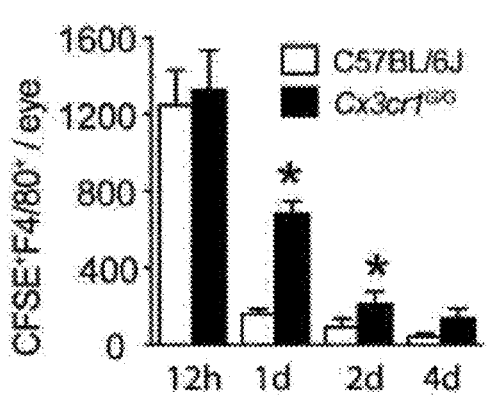
FIG. 33 is a histogram showing the results of the quantification of $CSFE^+F4/80^+$ Mφs at different time points after subretinal injections of C57BL/6J and $Cx3cr1^{GFP/GFP}$ $rCSFE^+$ Mφs. (n=0.5/per group (12 h) and n=6/per group thereafter, Mann & Whitney t test, *C57BL/6J vs. $Cx3cr1^{GFP/GFP}$ 1 d n=20/group p<0.0001; 2 d n=6/group p=0.0317).
Figure 34:
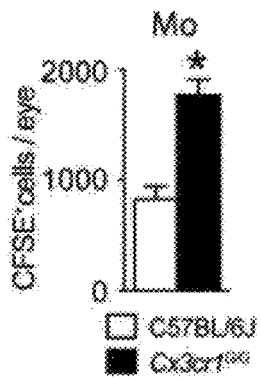
FIG. 34 is a histogram showing the results of the quantification of subretinal $CSFE^+$cells on RPE and retinal flatmounts 24 h after subretinal injections of $CSFE^+$ magnetic-bead-sorted bone marrow-derived monocytes (Mo) from C57BL/6J and $Cx3cr1^{GFP/GFP}$ mice into C57BL/6J mice (n=8-12/group; Mann & Whitney t tests; p=0.0006).
Figure 35:
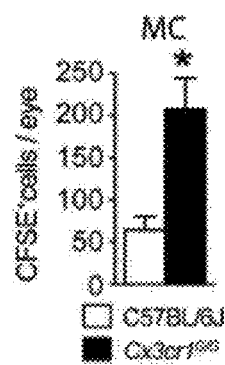
FIG. 35 is a histogram showing the results of the quantification of subretinal CSFE+cells on RPE and retinal flatmounts 24 h after subretinal injections of CSFE+ CD11bFACS-sorted brain MCs from C57BL/6J and Cx3cr1$^{GFP/GFP}$ mice into C57BL/6J mice (n=9-12/group; Mann & Whitney t tests; p=0.0087).

Quantifications showed that injected macrophages were quickly cleared from the subretinal space (FIG. 9), and clearance of the macrophages of both genotypes was achieved over a period of four days. Cytometric quantification of CFSE$^+$F4/80$^+$CD11b$^+$ macrophages in eye cell suspensions showed that Cx3cr1$^{GFP/GFP}$ macrophages are present in the eyes in significantly higher numbers 24 h after the injection (FIG. 10). CFSE$^+$F4/80$^+$ macrophages cell counts on Retinal pigment epithelium/choroidal and retinal flatmounts confirmed this difference in the subretinal space (FIG. 11). The CFSE fluorescence intensity of the F4/80$^+$CD11b$^+$-Mϕs in the cytometric analysis was strong and homogeneous (FIG. 10), suggesting that CFSE uptake by host cells (which leads to variable CFSE intensities), or proliferation (which leads to cell populations with halved CFSE fluorescence intensity) did not occur to a significant degree. Nevertheless, the clearance of Cx3cr1$^{GFP/GFP}$-Mϕs was significantly slower and Cx3cr1$^{GFP/GFP}$-Mϕs subsisted in significantly high numbers at one and two days (FIG. 33). No signs of egress from the subretinal space could be detected in WT- or Cx3cr1$^{GFP/GFP}$-Mϕs injected animals as no CFSE$^+$ cells were observed in the inner retina and choroid, blood, local lymph nodes, lung, liver, or spleen by histology or cytometry (data not shown). However, the nuclei of a large number of subretinal CFSE$^+$ cells were found to be TUNEL$^+$, and displayed signs of apoptosis such as pyknotic and fractioned nuclei, and were Annexin-V positive, but propidium iodide (PI) negative. Experiments were conducted to evaluate whether the observed differences were specific to peritoneal Mϕs or shared by MPs of other origins. CFSE-labeled, magnetic-bead-sorted bone marrow derived Mos (~95% pure, FIG. 34), and CD11bFACS-sorted brain MCs (~95% pure. FIG. 35) from WT and Cx3cr1$^{GFP/GFP}$ mice were adoptively transferred into the subretinal space of WT-mice. As with peritoneal Mϕs, Cx3cr1-deficient MPs of both origins were significantly greater in number when counted on retinal and RPE/choroidal flatmounts 1 d after the injections. Furthermore. WT- and Cx3cr1$^{GFP/GFP}$-Mϕs did not reveal differences in proliferation in vitro (FIG. 43), suggesting that fast proliferation of Cx3cr1$^{GFP/GFP}$-Mϕs does not account for the observed difference in the adoptive transfer experiments.

Figure 36:
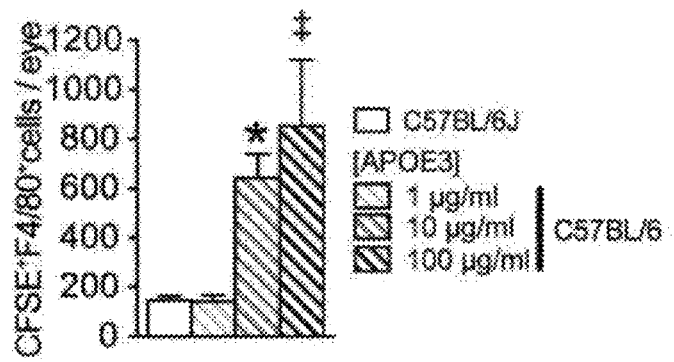
FIG. 36 is a histogram showing the results of the quantification of subretinal CSFE+F4/80+ Mφs on RPE and retinal flatmounts 24 h after subretinal injections of C57BL/6J CSFE+ Mφs into C57BL/6J and with exogenously added APOE3 at 1, 10 or 100 μg/mL calculated intraocular concentrations (n=6-7/group; One-way ANOVA/Dunnett test; C57BL/6J vs. 10 μg p=0.0488; C57BL/6J vs. 100 μg p=0.006. Mann & Whitney t tests; C57BL/6J vs. 10 μg p=0.0012; C57BL/6J vs. 100 μg p=0.0013).

To evaluate whether MP APOE expression influences the rate of subretinal MP clearance, Cx3cr1$^{GFP/GFP}$ApoE$^{-/-}$-Mϕs were adoptively transferred into WT-recipients. Strikingly, the increased resistance to subretinal clearance of Cx3cr1$^{GFP/GFP}$-Mϕs was completely eliminated with Cx3cr1$^{GFP/GFP}$ ApoE$^{-/-}$-Mϕs (FIG. 11). Furthermore, exogenous lipid-free APOE3, the predominant human APOE isoform, was sufficient to increase resistance to subretinal clearance when added to WT-CFSE$^+$-Mϕs (FIG. 36).

Taken together, these results show that subretinal macrophages clearance is predominantly mediated by apoptosis, as would be expected in a site of immune privilege, and in accordance with observations of inflammation resolution in peripheral tissue (Gautier et al., 2013) and in particular with leukocyte clearance in the context of the subretinal immunosuppressive environment (Streilein et al., 2002). Further, these results show that Cx3cr1-deficient MPs of all origins studied (peritoneum, bone marrow, and brain) are more resistant to subretinal clearance. This increase of resistance to clearance is APOE-dependent and that local, recombinant APOE is sufficient to inhibit WT-Mϕs elimination from the subretinal space.

Example 6

ApoE Controls Subretinal Macrophage Survival Via FasL

CX3CL1/CX3CR1 signaling is well known for its role in chemotaxis. Therefore, one might suspect inefficient egress to be at the origin of subretinal mononuclear phagocyte accumulation in Cx3cr1$^{GFP/GFP}$ mice. However, the present results show that mononuclear phagocyte egress does not measurably occur from the subretinal space, which is not surprising for an immune privileged site.

To test whether an alteration of the Retinal pigment epithelium immunosuppressive environment is associated with subretinal Cx3cr1$^{GFP/GFP}$ mononuclear phagocyte accumulation, FasL expression is first analyzed in vivo. The RPE constitutively expresses FasL (CD95L), which in part mediates its immunosuppressiveness (Wenkel & Streilein, 2000). RT-PCRs performed on Retinal pigment epithelium/choroidal extracts of 2 months- and 12 months-old C57BL/6J and Cx3cr1$^{GFP/GFP}$ mice showed that FasL mRNA expression is comparable in young mice, increase with age in Cx3cr1$^{+/+}$ mice, but is significantly lower in age-matched Cx3cr1$^{GFP/GFP}$ mice in which subretinal APOE-expressing mononuclear phagocytes accumulate (FIG. 12). Similarly, 2-month-old light-challenged Cx3cr1$^{GFP/GFP}$ mice with subretinal MP accumulation expressed significantly less FasL mRNA as compared to WT (data not shown).

Figure 17:
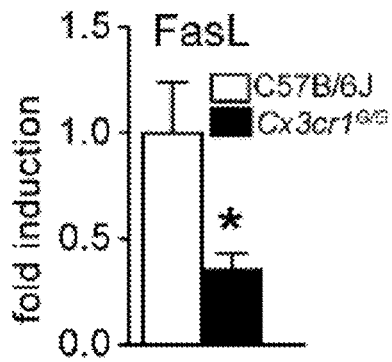
FIG. 17 is a histogram showing the levels of FasL mRNA measured by quantitative RT-PCR and normalized with β-actin mRNA of 12 months-old C57BL/6J Retinal pigment epithelium/choroid plexus 3 h after subretinal injection of C57BL/6J or $Cx3cr1^{GFP/GFP}$ TPCs (n=7-9 per group, *MWt at 12 months p=0.0129).

Immunohistochemistry on retinal sections and Retinal pigment epithelium flatmounts of WT mice and Cx3cr1$^{GFP/GFP}$ mice confirmed the diminished FasL expression in the Retinal pigment epithelium of Cx3cr1$^{GFP/GFP}$ mice with subretinal IBA-1$^+$ mononuclear phagocytes at 12 months (data not shown), thus suggesting that Cx3cr1-deficient MPs inhibit RPE-FasL transcription. This was confirmed by injecting Cx3cr1$^{GFP/GFP}$-Mϕs into the subretinal space of WT-mice, which showed that FasL transcription on RPE/choroidal extracts was significantly inhibited after 3 h, when compared to WT-Mϕs injected eyes (FIG. 17).

Figure 37:
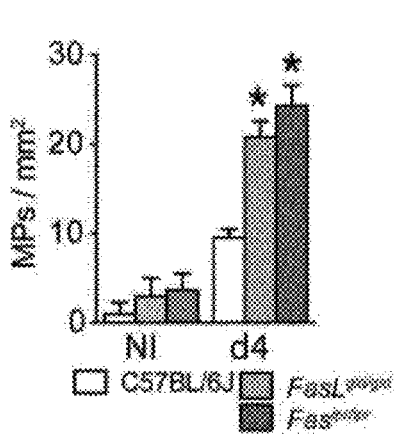
FIG. 37 is a histogram showing the results of the quantification of subretinal IBA-1+MPs in control (left) and four day light-challenged (right) 2 m-old mice of the indicated strains (n=6-10/group ANOVA/Dunnett test at 4 d light-challenge: C57BL/6J vs. FasL$^{gld/gld}$ and C57BL/6J vs. Fas$^{lpr/lpr}$ both *p<0.0001; Mann & Whitney t test at 4 d light-challenge; C57BL/6J vs. FasL$^{gld/gld}$ *p<0.0001; C57BL/6J vs. Fas$^{lpr/lpr}$ *p<0.0001).

FasL is known to induce the apoptosis of activated monocytes and activated macrophages in vitro but its role in the clearance of subretinal mononuclear phagocytes remains unknown. To evaluate whether FAS-FASL signaling participates in MP clearance, subretinal MP numbers were compared in light-challenged WT-, FASL-defective- (FasL$^{gld/gld}$-mice) and FAS-defective- (Fas$^{lpr/lpr}$-mice) (FasL$^{gld/gld}$- and Fas$^{lpr/lpr}$-mice develop lymphadenopathy and systemic autoimmune disease with age, making it difficult to evaluate age-dependent MP accumulation at 12-months). Quantification of subretinal IBA1$^+$-MPs on retinal and RPE/choroidal-flatmounts revealed a significant increase of subretinal MPs in 2-months-old FasL$^{gld/gld}$- and Fas$^{lpr/lpr}$-mice induced by four days of light-challenge (FIG. 37), similar to that of Cx3cr1$^{GFP/GFP}$ mice.

Adoptive transfer experiments in which WT CFSE$^+$ TPCs were subretinally injected into C57BL/6J (WT) or FasL-defective mice (FasL$^{gld/gld}$ mice), and Fas-defective CFSE$^+$ TPCs (prepared from thioglycollate-elicited peritonitis Fas$^{lpr-lrp}$ mice) into C57BL/6J mice, reveal that subretinal CFSE$^+$F4/80$^+$ macrophages are significantly more numerous 24 h after the injection when Fas or FasL function is impaired and similar to the numbers of Cx3cr1$^{GFP/GFP}$-CFSE$^+$ macrophages in WT recipients at 24 h (FIG. 13).

Figure 21:
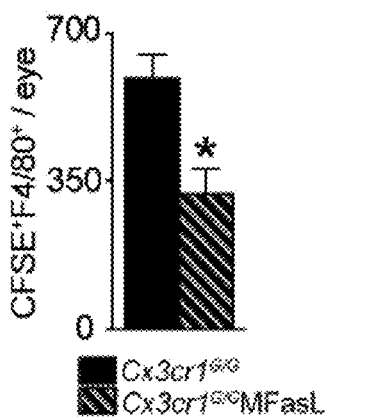
FIG. 21 is a histogram showing the quantification of subretinal $CFSE^+F4/80^+$ macrophages on Retinal pigment epithelium and retinal flatmounts 24 h after subretinal injection of $Cx3cr1^{GFP/GFP}$ $CFSE^+$ TPCs into C57BL/6J with or without the Fas agonist MegaFasL (calculated intraocular concentrations 10 ng/mL; n=7-8 per group, *MWt p=0.014).
Figure 38:
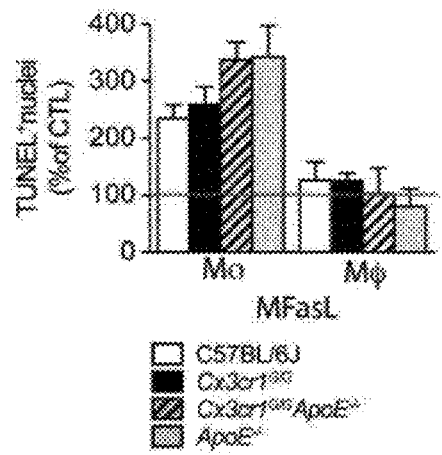
FIG. 38 is a histogram showing the results of the quantification of in vitro MegaFasL-induced apoptosis of Mos and Mφs of the indicated genotypes (C57BL/6J, Cx3cr1$^{GFP/GFP}$, Cx3cr1$^{GFP/GFP}$ApoE$^{-/-}$ and ApoE$^{-/-}$) cultured for 24 h, TUNEL+ quantification are expressed as percentage of non MegaFasL exposed control.

To test whether differences in the susceptibility to FASL-induced MP death might contribute to the protective effect of ApoE-deletion in subretinal MP accumulation, monocytes (Mos) and thioglycollate-elicited Mϕs from the different mouse strains were exposed to MegaFasL and TUNEL$^+$ cells were quantified at 24 h in vitro (FIG. 38). The results show that FASL is sufficient to induce Mos apoptosis in vitro in comparison to Mϕs, which are rather resistant to FASL-induced apoptosis in vitro (Kiener et al, 1997; Park et al, 2003; Um et al, 1996). No difference was observed between wildtype- and Cx3cr1$^{GFP/GFP}$-cells of either Mos or Mϕs, but a tendency toward increased susceptibility in Mos of both Cx3cr1$^{GFP/GFP}$ ApoE$^{-/-}$- and ApoE$^{-/-}$-cells, which might contribute toward the differences in clearance observed in vivo. These results also highlight that FASL acts along with other factors in vivo to induce Mϕ apoptosis in the subretinal space, as the effect of MegaFasL on subretinally clearance of adoptively transferred peritoneal Mϕs (FIG. 21) was much stronger than MegaFasL-induced apoptosis in vitro (FIG. 38).

These results show that Retinal pigment epithelium Fas-FasL signaling participates in subretinal macrophage clearance in vivo, and that subretinal Cx3Cr1$^{GFP/GFP}$-MPs are associated with a downregulation of RPE FASL expression, and that substitution by MegaFasL restores, the clearance of subretinal Cx3cr1$^{GFP/GFP}$-MPs.

Example 7

APOE Promotes Subretinal Macrophage Survival Via IL-6

IL-6 is known to downregulate FasL transcription in lymphocytes. Further, APOE and APOA-I are known for their capacity to either activate TLR signaling, or inhibit LPS/TLR4 induced IL-6 induction. APOE and APOA-I can both activate the CD14-dependent innate immunity receptor cluster that contains TLR-2 and -4 in the absence of TLR Ligands (Smoak et al., 2010). This activation has been shown to induce IL-6, among other cytokines, in the case of APOA-I. The present results confirm that APOA-I and APOE3 significantly inhibit LPS-induced IL-6 secretion of macrophages in vitro, measured by ELISA of the supernatants 8 h after stimulation (FIG. 14). Similarly, upon incubation of WT-peritoneal-Mϕs with recombinant lipid-free APOE3 for 24 h, IL-6 was very significantly induced (FIG. 39). The LPS inhibitor Polymyxin B did not inhibit the induction, while 90 min heat-denaturation abolished the induction, confirming that LPS contamination of APOE3 is not accountable for the effect, as shown for APOA-I using multiple approaches (Smoak et al, 2010). As shown for APOA-I, this induction was largely CD14- and TLR2-dependent, as neutralizing antibodies inhibited this effect, when compared to a control IgG (FIG. 39).

However, lipid-free APOE3 and APOA-I when administered without TLR agonists such as LPS, also are significantly inducing IL-6 in macrophages at 8 h (FIG. 14) as previously reported for APOA-1. At 24 h, IL-6 secretion further increases in APOE3 stimulated macrophages, while 90 min heat-denaturation (95° C.) abolishes the induction, confirming that LPS contamination of APOE3 is not accountable for the effect, as shown for APOA-1 using multiple approaches.

Correspondingly, Cx3cr1$^{GFP/GFP}$ TPMs express and secrete significantly higher amounts of IL-6 compared to WT TPMs (FIGS. 15 and 16) when cultured 24 h with CX3CL1. This effect is significantly inhibited in Cx3cr1$^{GFP/GFP}$ ApoE$^{-/-}$ TPMs as observed by RT-PCR (FIG. 15) and ELISA (FIG. 16). Although IL-6 is not detectable by RT-PCR in whole eye mRNA extracts in vivo, IL-6 staining is reproducibly detected in IBA-1$^+$ subretinal mononuclear phagocytes in 12 months-old Cx3cr1$^{GFP/GFP}$ mice and light-challenged Cx3cr1$^{GFP/GFP}$ mice (data not shown). These results show that exogenous APOE and APOE overexpressing Cx3cr1$^{GFP/GFP}$ macrophages produce increased amounts of IL-6.

To test whether ApoE-IL-6 secreting macrophages directly affect Retinal pigment epithelium FasL expression, WT and Cx3cr1$^{GFP/GFP}$ TPCs are injected subretinally into WT recipients and Retinal pigment epithelium FasL mRNA expression is evaluated by RT-PCR on Retinal pigment epithelium/choroidal extracts after 3 hours. Indeed, Cx3cr1$^{GFP/GFP}$ TPCs significantly inhibit FasL transcription when compared to WT TPCs injected eyes (FIG. 17).

Figure 18:
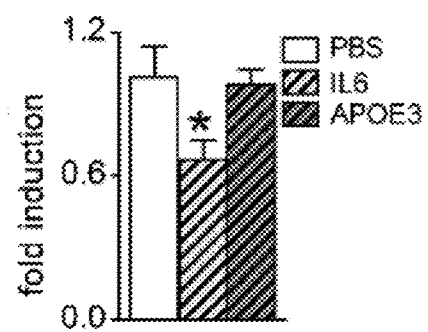
FIG. 18 is a histogram showing the levels of FasL mRNA measured by quantitative RT-PCR and normalized with β-actin mRNA of 12 months-old C57BL/6J Retinal pigment epithelium/choroid plexus 3 h after subretinal injection of IL-6 and APOE3 (calculated intraocular concentrations 50 µg/mL and 10 µm respectively; n=17-21 per group, *MWt IL-6 vs. control (CTL) p=0.0148).

In fact, subretinal injection of recombinant IL-6 is sufficient to significantly inhibit Retinal pigment epithelium FasL transcription in vivo compared to PBS. In contrast, lipid-free APOE3, injected at a dose sufficient to induce increased subretinal macrophages survival (FIG. 18), does not alter FasL expression directly, when injected without macrophages. These results suggest that macrophages IL-6, but not APOE, regulates Retinal pigment epithelium FasL expression.

Figure 19:
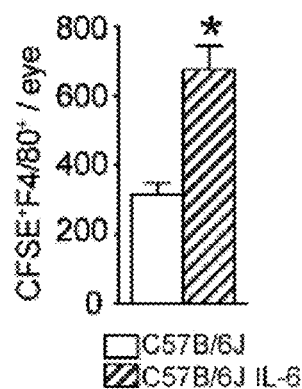
FIG. 19 is a histogram showing the quantification of subretinal $CFSE^+F4/80^+$ macrophages on Retinal pigment epithelium and retinal flatmounts 24 h after subretinal injection of C57BL/6J $CFSE^+$ TPCs into C57BL/6J with or without IL-6 (calculated intraocular concentrations of 50 ng/mL; n=7-12 per group, *MWt p<0.0001).
Figure 20:
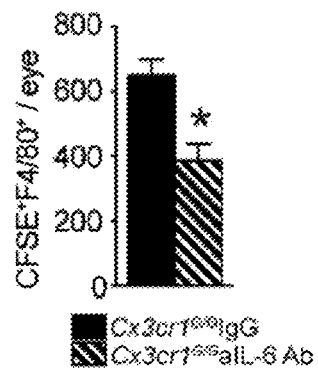
FIG. 20 is a histogram showing the quantification of subretinal $CFSE^+F4/80^+$ macrophages on Retinal pigment epithelium and retinal flatmounts 24 h after subretinal injection of $Cx3cr1^{GFP/GFP}$ $CFSE^+$ TPCs into C57BL/6J with control-, or anti-IL-6 antibody (calculated intraocular concentrations of 50 µg/mL n=8-12 per group, *MWt p=0.0036).
Figure 22A:
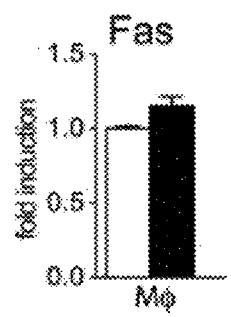
FIG. 22A is a histogram showing the levels of FAS mRNA measured by quantitative RT-PCR and normalized with S26 mRNA of C57BL/6J and $Cx3cr1^{GFP/GFP}$ PEM cultured for 24 h with CX3CL1 (n=4 per group).
Figure 22B:
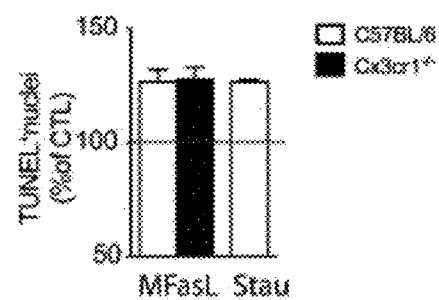
FIG. 22B is a histogram showing the levels of apoptotic cell death by TUNEL+quantification of C57BL/6J and $Cx3cr1^{GFP/GFP}$ PEM cultured for 24 h with MegaFasL (10 ng/mL) and Staurosporin, expressed as a percentage of control.

In addition, recombinant IL-6 added to CFSE+TPCs more than doubles the number of subretinal WT CFSE+F4/80+ macrophages (FIG. 19) and an IL-6 blocking antibody significantly decreases subretinal $Cx3cr1^{GFP/GFP}$CFSE+F4/80+ macrophages (FIG. 20) 24 h after injection compared to their controls. Further, CD14- and IL-6 blocking antibodies decreases subretinal IBA-1+MPs/impact localized on the lesion surrounding RPE of $Cx3cr1^{GFP/GFP}$ mice (FIG. 40). Furthermore, co-administration of the hexameric Fas agonist MegaFasL (Greaney et al., 2006) to $Cx3cr1^{GFP/GFP}$CFSE+ TPCs efficiently compensates for the observed FasL downregulation (FIG. 21) and significantly reduces the number of subretinal $Cx3cr1^{GFP/GFP}$CFSE+F4/80+ macrophages similarly to the IL-6 blocking antibody. Fas RT-PCRs and Fas induced apoptosis performed on WT and $Cx3cr1^{GFP/GFP}$ macrophage in vitro does not reveal any difference between the genotypes (FIGS. 22A and 22B), thereby indicating that discrepancies in subretinal macrophage survival is not due to altered susceptibility of $Cx3cr1^{GFP/GFP}$ macrophages to FasL/Fas induced apoptosis.

To test whether CD14-dependent IL-6 induction does indeed participate in subretinal MP accumulation in vivo, control IgG and IL-6- or CD14-neutralizing antibody were injected into the vitreous of $Cx3cr1^{GFP/GFP}$ mice after induction of subretinal inflammation with a laser-injury (which also facilitates antibody penetration to the subretinal space). The accumulation of subretinal IBA1+MPs observed on the RPE adjacent to CD102+CNV seven days after a laser-impact was significantly inhibited when CD14 or IL-6 was neutralized, as was the associated CNV (FIG. 42).

In summary, the present data show that macrophage APOE regulates macrophage IL-6 expression and that Retinal pigment epithelium FasL, regulated by IL-6, is an important mediator of subretinal macrophage clearance. This mechanism explains how endogenous APOE of $Cx3cr1^{GFP/GFP}$ macrophages and exogenously added APOE to WT macrophages increases mononuclear phagocytes survival in the subretinal space. $Cx3cr1^{GFP/GFP}$ MPs thus express increased amounts of APOE. APOE induces the expression of IL-6 in MPs, which in turn downregulates FasL transcription in the RPE. The diminished FASL expression participates in the increased survival time of subretinal $Cx3cr1^{GFP/GFP}$ MPs.

The present results thereby demonstrate for the first time that APOE and IL-6 participate in AMD pathogenesis. Considering that IL-6 was shown to repress RPE FasL expression, to prolong subretinal MP survival and to promote chronic subretinal inflammation, CD14 or IL-6 inhibition is thus capable to help reestablish RPE immune-suppressive function and inhibit pathogenic inflammation in late AMD.

Example 8

Figure 23:
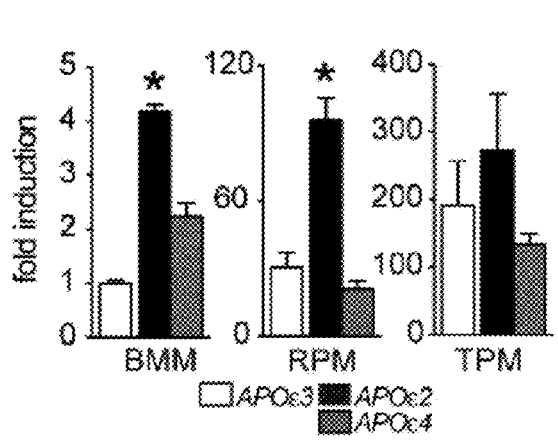
FIG. 23 is a histogram showing the levels of ApoE mRNA measured by quantitative RT-PCR and normalized with S26 mRNA of transgenic humanized APOε3, APOε2 and APOε4 for 24 h cultured BMMs, macrophages and PEM (n=6 per group, BMM *MWt ε2 vs. ε3 p=0.0047; resident macrophages *MWt ε2 vs. ε3 p=0.0022).
Figure 24:
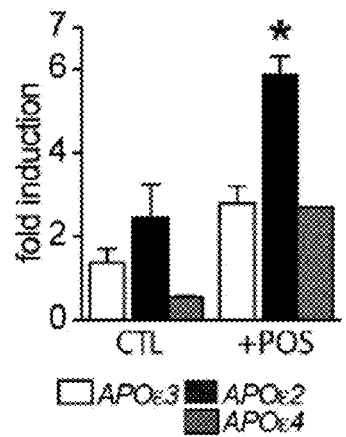
FIG. 24 is a histogram showing the levels of ApoE mRNA measured by quantitative RT-PCR and normalized with S26 mRNA of transgenic humanized APOε3, APOε2 and APOε4 for 3 days (3 d) cultured BMMs with and without POS (n=6 per group, BMM *MWt ε2 vs. ε3 p=0.0022).

APOε2 Allele Associated ApoE Secretion Promotes Subretinal Macrophages Survival and Retinal Degeneration As shown above, CX3CR1 regulates APOE transcription in mononuclear phagocytes, but the transcriptional regulation of APOE is complex and is known to require the interaction of transcription factors with the proximal promoter and distal enhancers. Two polymorphisms that define the ε2/ε3/ε4 alleles, rs7412 and rs429358, have recently been shown to be imbedded in a well-defined CpG island that regulates APOE transcription epigenetically in a cell type-, isoform- and DNA methylation-dependent manner (Yu et al., 2013). The APOε2 allele that confers an increased AMD risk lacks a CpG site at rs7412 when compared to other isoforms, leading to increased APOE transcription in certain cell types such as brain astrocytes. To evaluate the influence of the APOE allele on its transcription in mononuclear phagocytes, a humanized APOE mouse model with a CpG island structure identical to human APOE isoforms is employed. The results show that APOε2 BMMs and RPM express significantly more APOE mRNA compared to the two other isoforms after 24 h of cell culture (FIG. 23, calculated relatively to APOε3 BMMs). The expression in TPMs is more variable and no significant difference is detected in freshly extracted brain MCs (data not shown). Similarly. RT-PCRs of APOε2 BMMs cultured for 3 days in the presence of POS, to simulate subretinal mononuclear phagocyte differentiation, express significantly more APOE mRNA when compared to BMMs from APOε3, and APOε4 mice (FIG. 24).

Figure 25:
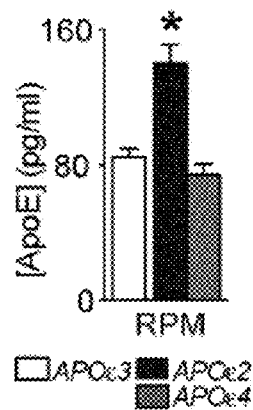
FIG. 25 is a histogram showing the results of human APOE ELISA of 24 h supernatants from humanized APOε3, APOε2 and APOε4 macrophages (n=6, *MWt ε2 vs. ε3 p=0.0041).

Interestingly, unlike BMMs cultured for 24 h, no significant difference is detected in BMMs cultured without POS at 3 days, similar to a known previous report of 14 days in vitro monocyte-derived macrophages from human donors homozygous for each APOE isoforms. APOε2 RPMs also secrete significantly more APOE when compared to the other isoforms, as determined using an anti-human APOE ELISA (FIG. 25). Interestingly, Cx3cr1 deficiency and the APOε2 allele does not affect APOE transcription in the same mononuclear phagocytes, suggesting that the underlying transcriptional regulatory mechanisms are distinct. However, Cx3cr1 deficiency and the APOε2 allele affect APOE transcription in POS-incubated BMMs that possibly best simulates subretinal mononuclear phagocyte differentiation of infiltrating monocytes.

Figure 26:
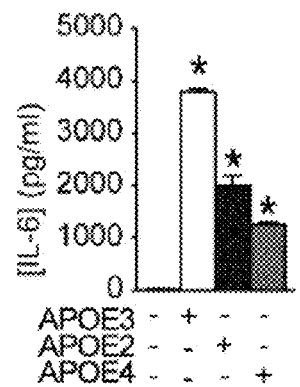
FIG. 26 is a histogram showing the results of mouse IL-6 ELISA of supernatants of C57BL/6J macrophages at 24 h cultured in control condition or with APOE3, APOE2, APOE4 (5 µg/mL, n=10-12, *MWt CTL vs. APOE3 p<0.001; ‡*MWt CTL vs. APOE2 p<0.0001).
Figure 27:
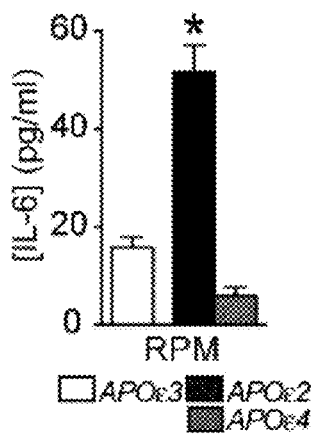
FIG. 27 is a histogram showing the results of mouse IL-6 ELISA of supernatants of macrophages from APOε3, APOε2 and APOε4 mice (n=12 per group, *MWt ε2 vs. ε3 p<0.0001).

As APOE-dependent macrophage IL-6 secretion is an important mediator of increased subretinal macrophage survival, it is tested whether the APOE isoforms induce IL-6 similarly and whether ε2/ε3/ε4 allele bearing macrophages differ in IL-6 release in vitro. ELISA analysis of culture media from APOE-incubated C57BL/6J RPMs show that all three isoforms significantly induce IL-6 secretion when compared to control, but the induction by APOE2 and APOE4 is significantly inferior to APOE3 (FIG. 26). However, APOε2 RPMs, that secrete increased amounts of APOE, release significantly more IL-6 when compared to APOε3 and APOε4 macrophages (FIG. 27).

These results show that the decreased efficiency of APOE2 in inducing IL-6 is more than compensated by the increase in APOE secretion in APOε2 RPM.

To test whether the increased APOE and IL-6 secretion observed in APOε2 RPM lead to decreased subretinal macrophage clearance, CFSE-labeled resident peritoneal cavity cells (RPC) are injected subretinally and CFSE+F4/80+ macrophages are quantified on retinal and Retinal pigment epithelium flatmounts at 24 h.

Figure 28:
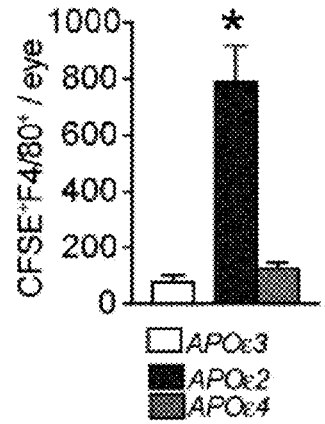
FIG. 28 is a histogram showing the results of the quantification of subretinal $CFSE^+F4/80^+$ macrophages on Retinal pigment epithelium and retinal flatmounts 24 h after subretinal injection of CFSE-stained RPC from APOε3, APOε2 and APOε4 mice into C57BL/6J mouse eyes (n=8-12 per group, *MWt p<0.0001).
Figure 29:
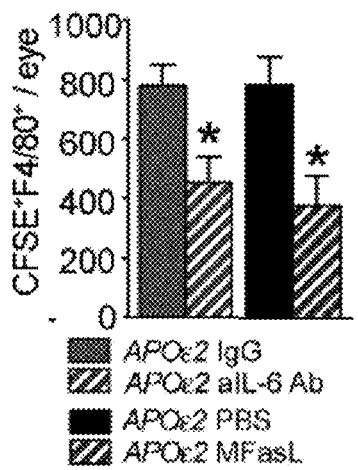
FIG. 29 is a histogram showing the results of the quantification of subretinal $CFSE^+F4/80^+$ macrophages on Retinal pigment epithelium and retinal flatmounts 24 h after subretinal injection of CFSE-stained RPC from APOε2 $CFSE^+$ RPCs with control, or anti-IL-6 antibody (n=16-20 per group, *MWt p=0.0024) and with or without MegaFasL (n=7-12 per group, *MWt p=0.015).

APOε2 RPMs were significantly more numerous than APOε3 and APOε4 Macrophages (FIG. 28), and addition of IL-6 blocking antibody or MegaFasL significantly reduced APOε2 macrophages presence 24 h after the injection (FIG. 29).

Figure 30:
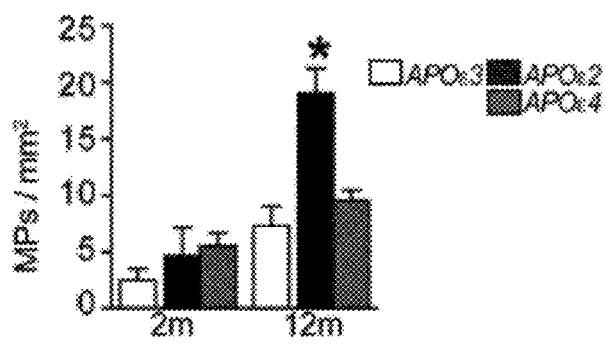
FIG. 30 is a histogram showing the results of the quantification of subretinal IBA-1+ mononuclear phagocytes in 2 months and 12 months-old APOε3, APOε2 and APOε4 mice (n=12 per group, *ANOVAB ε2 vs. ε3 and ε4 at 12 months p<0.003).
Figure 44:
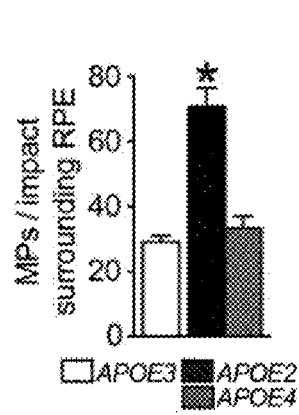
FIG. 44 is a histogram showing the quantification of subretinal IBA-1+MPs/impact localized on the lesion surrounding RPE of APOE3, APOE2 and APOE4 mice at d7 after laser-injury (n=8-9/group, One way ANOVA/Bonferroni post-hoc tests *APOE3 vs APOE2 p=0.0004. Mann & Whitney t test *APOE2 vs APOE3 p=0.0004)
Figure 48:
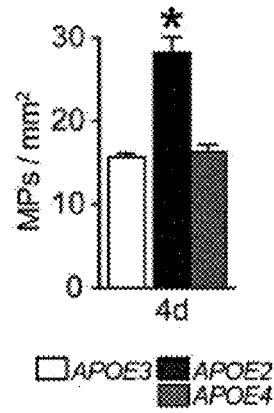
FIG. 48 is a histogram showing Quantification of subretinal IBA-1+MPs after four days of light-challenge of 2 m-old mice of the indicated strains (n=6/group ANOVA/Bonferroni *APOE3 vs APOE2 p=0.0007; Mann & Whitney t test of APOE3 vs APOE2 p=0.0022).

To study whether the APOε2 allele confers this resistance to subretinal mononuclear phagocyte clearance in vivo, we evaluated mononuclear phagocyte accumulation on IBA-1 stained retinal and Retinal pigment epithelium/choroidal flatmounts of 12 months-old APOε3-, APOε2-, and APOε4-mice. Interestingly, quantification of subretinal IBA-1 mononuclear phagocytes showed a significant age-dependent subretinal mononuclear phagocyte accumulation in APOε2 mice compared to mice carrying the other isoforms (FIG. 30). Furthermore, this significant increase of subretinal MPs was observed in APOε2-mice 4 days after a 4500 lux light-challenge (FIG. 48) and 7 days after the induction of subretinal inflammation by a laser burn (FIG. 44).

Figure 31A:
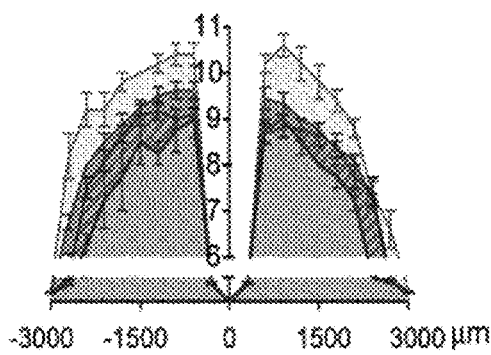
FIG. 31A is a graph showing the photoreceptor nucleus rows at increasing distances (−3000 µm: inferior pole, +3000 µm: superior pole) from the optic nerve (0 µm) in 12 months-old APOε3, APOε2 and APOε4 mice.
Figure 31B:
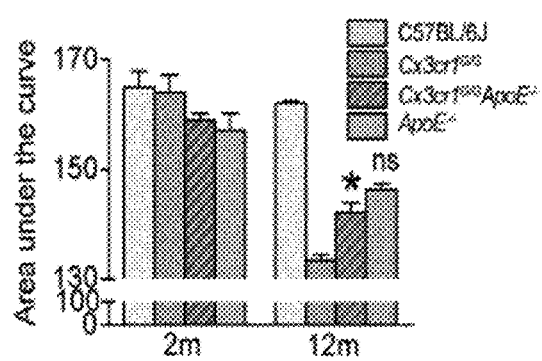
FIG. 31B is a histogram showing the results of the quantification of the area under the curve of photoreceptor nucleus row counts of 2 and 12 months-old APOε3, APOε2 and APOε4 mice (n=6, *MWt ε2 vs. ε3 at 12 months p=0.016; *ANOVAB ε2 different from ε3 and ε4 mice at 12 months p=0.0029).
Figure 46:
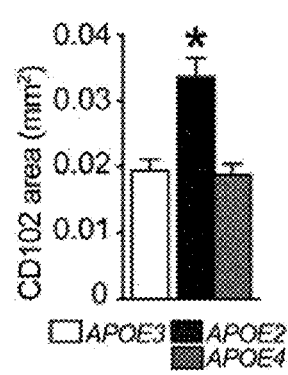
FIG. 46 is a histogram showing the quantification of CD102+CNVs at d7 after laser-injury of APOE3, APOE2 and APOE4 mice (n=8-9/group, One-way ANOVA/Bonferroni post-hoc tests *APOE2 vs APOE3 p=0.0001, Mann & Whitney t test; *APOE2 vs APOE3 at 12 m p=0.0004).

Moreover, histological analysis of 12 months-old APOε3-, APOε2- and APOε4-mice and quantification (FIGS. 31A and 31B) of their ONL thickness reveal a significant age-dependent loss of photoreceptors in 12 months-old APOε2 mice, compared to APOε3 and APOε4-mice and the increased inflammation in APOε2-mice 7 d after laser-injury was accompanied by increased choroidal neovascularization, quantified as CD102 positive area on RPE/flatmounts (FIG. 46).

Moreover, histological analysis of 12 months-old APOε3-, APOε2- and APOε4-mice and quantification (FIGS. 31A and 31B) of their ONL thickness reveal a significant age-dependent loss of photoreceptors in 12 months-old APOε2 mice, compared to APOε3- and APOε4-mice.

Figure 45:
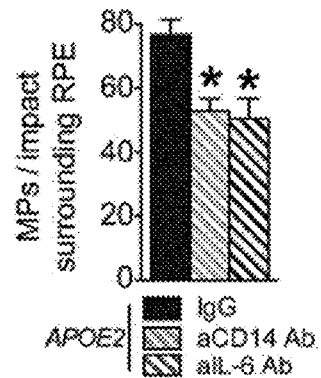
FIG. 45 is a histogram showing the quantification at d7 after laser-injury of subretinal IBA-1+MPs/impact localized on the lesion surrounding RPE of APOE2 mice injected with control IgG, or IL-6 and CD14 blocking antibodies (calculated intraocular concentration 5 μg/ml; n=13-14/group. One way ANOVA/Dunnett's post-hoc tests of IgG vs any other group *p<0.001. Mann & Whitney t test *IgG vs anti IL-6 p=0.0028; IgG vs anti CD14 p=0.0021).
Figure 47:
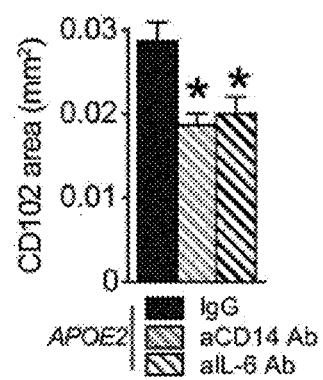
FIG. 47 is a histogram showing the quantification of CD102+CNVs at d7 after laser-injury of APOE2 mice injected with control IgG or IL-6 and CD14 blocking antibody (calculated intraocular concentration 5 μg/ml; n=13-14/group. One way ANOVA/Dunnett's post-hoc tests of IgG vs any other group *p<0.01, Mann & Whitney t test *IgG vs anti IL-6 p=0.0029; IgG vs anti CD14 p=0.0012).

To test whether CD14-dependent IL-6 induction does indeed participate in subretial MP accumulation in vivo, control IgG and IL-6- or CD14-neutralizing antibody were injected into the vitreous of APOε2-mice after induction of subretinal inflammation with a laser-injury (which also facilitates antibody penetration to the subretinal space). The accumulation of subretinal IBA1+MPs observed on the RPE adjacent to CD102+CNV seven days after a laser-impact was significantly inhibited when CD14 or IL-6 was neutralized (FIG. 45), as was the associated CNV (FIG. 47) similar to Cx3cr1$^{GFP/GFP}$ mice.

In summary, the above results show that the AMD-risk conferring APOε2 allele is associated with increased APOE transcription and IL-6 secretion in mononuclear phagocytes under certain circumstances. The above experiments demonstrate that APOE-overexpressing APOε2 mononuclear phagocytes are more resistant to subretinal clearance in an IL-6 and FasL-dependent fashion. It can thus be inferred from the age-dependent accumulation of subretinal mononuclear phagocytes and associated photoreceptor degeneration observed in aged APOε2 transgenic mice in vivo that a similar mechanism is taking place under the retina in vivo.

Considered collectively, the above findings provide an important pathomechanism for the yet unexplained association of elevated IL-6 levels with AMD (Klein et al., 2008), demonstrate that the accumulation of subretinal mononuclear phagocytes in and around soft drusen are involved in the significant focal inflammation observed in early intermediate AMD. These findings also demonstrate that APOE is expressed in subretinal mononuclear phagocytes in early AMD, and increased in mice lacking the tonic inhibitory signal of CX3CR1 and in APOε2 transgenic mice. The above results demonstrate that APOE induces IL-6, which downregulates Retinal pigment epithelium FasL expression and thereby allows prolonged subretinal mononuclear phagocyte survival, mononuclear phagocyte accumulation, and the associated photoreceptor degeneration observed in Cx3Cr1 deficient mice and APOε2 mice.

The above results further demonstrate that the AMD-risk conferring APOε2 allele is associated with increased APOE transcription in mononuclear phagocytes, and that this mechanism is independent from CX3CR1 signaling. These results also show that APOE over-expressing subretinal mononuclear phagocytes, observed in APOε2 TR and Cx3cr1$^{GFP/GFP}$ mice, are more resistant to elimination. In view of these results, increased subretinal mononuclear phagocytes accumulation adjacent to Retinal pigment epithelium in APOε2 carrying patients around soft drusen, adjacent to geographic lesions and in CNV thus clearly appear to be involved in AMD progression and late AMD. It therefore results from what precedes that, surprisingly, inhibition of excess APOE and IL-6, or restoration of Retinal pigment epithelium FasL expression allows controlling the subretinal inflammation in early AMD and prevents the development of late AMD.

BIBLIOGRAPHY

Anderson et al. (2001) Local cellular sources of apolipoprotein E in the human retina and retinal pigmented epithelium: implications for the process of drusen formation. *Am J Ophthalmol* 131: 767-781.

Basu et al. (1982) Biochemical and genetic studies of the apoprotein E secreted by mouse macrophages and human monocytes. *J Biol Chem* 257: 9788-9795.

Brakenhoff et al. (1994) Development of a human interleukin=6 receptor antagonist. *J Biol Chem.* 269(1):86-93.

Camelo et al. (2012) Delta-like 4 inhibits choroidal neovascularization despite opposing effects on vascular endothelium and macrophages. *Angiogenesis* 15: 609-622.

Chang et al. (2013) Survey of common eye diseases in laboratory mouse strains. *Invest Ophthalmol Vis Sci* 54: 4974-4981.

Chen et al. (2013) Paraquat-Induced Retinal Degeneration Is Exaggerated in CX3CR1-Deficient Mice and Is Associated with Increased Retinal Inflammation. *Invest Ophthalmol Vis Sci* 54: 682-690.

Combadiere et al. (2007) CX3CR1-dependent subretinal microglia cell accumulation is associated with cardinal features of age-related macular degeneration. *J Clin Invest* 117: 2920-2928.

Combadière et al. (2003). Decreased atherosclerotic lesion formation in CX3CR1/apolipoprotein E double knockout mice. Circulation, 107(7):1009-16.

Gautier et al. (2013) Local apoptosis mediates clearance of macrophages from resolving inflammation in mice. *Blood* 122: 2714-2722.

Greaney et al. (2006) A Fas agonist induces high levels of apoptosis in haematological malignancies. *Leukemia research* 30: 415-426.

Gupta et al. (2003) Activated microglia in human retinitis pigmentosa, late-onset retinal degeneration, and age-related macular degeneration. *Exp Eye Res* 76: 463-471.

Hirata et al. (1989) Characterization of IL-6 receptor expression by monoclonal and polyclonal antibodies. J Immunol. 143(9):2900-6.

Houssier et al. (2008) CD36 deficiency leads to choroidal involution via COX2 down-regulation in rodents. *PLoS Med* 5: e39.

Kezic et al. (2013) The Effects of Age and Cx3cr1 Deficiency on Retinal Microglia in the Ins2Akita Diabetic Mouse. *Invest Ophthalmol Vis Sci* 54: 854-863.

Kiener et al. (1997) Differential induction of apoptosis by Fas-Fas ligand interactions in human monocytes and macrophages. *J Exp Med* 185: 1511-1516.

Klein et al. (2007) Fifteen-year cumulative incidence of age-related macular degeneration: the Beaver Dam Eye Study. *Ophthalmology.* 114(2):253-62.

Klein et al. (2008) Inflammation, complement factor h, and age-related macular degeneration: the Multi-ethnic Study of Atherosclerosis. *Ophthalmology* 115: 1742-1749.
Kohno et al. (2013) Photoreceptor Proteins Initiate Microglial Activation via Toll-like Receptor 4 in Retinal Degeneration Mediated by All-trans-retinal. *J Biol Chem* 288: 15326-15341.
Luhmann et al. (2012) Differential modulation of retinal degeneration by Ccl2 and Cx3cr1 chemokine signalling. *PLoS One* 7: e35551.
Ma et al. (2009) Microglia in the mouse retina alter the structure and function of retinal pigmented epithelial cells: a potential cellular interaction relevant to AMD. *PLoS One* 4: e7945.
Ma et al. (2011) Contribution of IL-17-producing gamma delta T cells to the efficacy of anticancer chemotherapy. J Exp Med. 14; 208(3):491-503.
Matsuda et al. (1998) Establishment of an interleukin 6 (IL 6)/B cell stimulatory factor 2-dependent cell line and preparation of anti-IL 6 monoclonal antibodies. *Eur J Immunol.* 18(6):951-6.
Molday et al. (1987) Peripherin. A rim-specific membrane protein of rod outer segment discs. *Invest Ophthalmol Vis Sci* 28: 50-61.
Nakai et al. (1996) Expression of apolipoprotein E mRNA in rat microglia. *Neurosci Lett* 211: 41-44.
Oh et al. (1999) The potential angiogenic role of macrophages in the formation of choroidal neovascular membranes. *Invest Ophthalmol Vis Sci* 40: 1891-1898.
Ong et al. (2001) Effects of cholesterol and apolipoprotein E on retinal abnormalities in ApoE-deficient mice. *Invest Ophthalmol Vis Sci* 42: 1891-1900.
Park et al. (2003) Fas (CD95) induces proinflammatory cytokine responses by human monocytes and monocyte-derived macrophages. *J Immunol* 170: 6209-6216.
Penfold et al. (1985) Senile macular degeneration: the involvement of immunocompetent cells. *Graefes Arch Clin Exp Ophthalmol* 223: 69-76.
Peri et al. (2008) Live imaging of neuronal degradation by microglia reveals a role for v0-ATPase a1 in phagosomal fusion in vivo. *Cell* 133: 916-927.
Ransohoff R M (2009) Chemokines and chemokine receptors: standing at the crossroads of immunobiology and neurobiology. *Immunity* 31: 711-721.
Raoul et al. (2008) Role of the chemokine receptor CX3CR1 in the mobilization of phagocytic retinal microglial cells. *J Neuroimmunol* 198: 56-61.
Rosenfeld et al. (1993) Abundant expression of apoprotein E by macrophages in human and rabbit atherosclerotic lesions. *Arterioscler Thromb* 13: 1382-1389.
Sather et al. (2007) A soluble form of the Mer receptor tyrosine kinase inhibits macrophage clearance of apoptotic cells and platelet aggregation. *Blood* 109: 1026-1033.
Sato et al. (1996) Humanization of an anti-human IL-6 mouse monoclonal antibody glycosylated in its heavy chain variable region. *Hum Antibodies Hybridomas.* 7(4):175-83.
Savino et al. (1994) Generation of interleukin=6 receptor antagonists by molecular-modeling guided mutagenesis of residues important for gp130 activation. EMBO J. 13(6): 1357-67.
Seddon et al. (2005) Progression of age-related macular degeneration: prospective assessment of C-reactive protein, interleukin 6, and other cardiovascular biomarkers. *Arch Ophthalmol* 123: 774-782.
Sennlaub et al. (2013) CCR2(+) monocytes infiltrate atrophic lesions in age-related macular disease and mediate photoreceptor degeneration in experimental subretinal inflammation in Cx3cr1 deficient mice. *EMBO Mol Med* 5: 1775-1793.
Silverman et al. (2003) Constitutive and inflammatory mediator-regulated fractalkine expression in human ocular tissues and cultured cells. *Invest Ophthalmol Vis Sci* 44: 1608-1615.
Smoak et al. (2010) Myeloid differentiation primary response protein 88 couples reverse cholesterol transport to inflammation. *Cell metabolism* 11: 493-502.
Streilein et al. (2002) Immunobiology and privilege of neuronal retina and pigment epithelium transplants. *Vision Res* 42: 487-495.
Tamura et al. (1993) Soluble interleukin=6 receptor triggers osteoclast formation by interleukin 6. Proc Natl Acad Sci USA. 90(24):11924-8.
Um et al. (1996) Fas mediates apoptosis in human monocytes by a reactive oxygen intermediate dependent pathway. *J Immunol* 156: 3469-3477.
Verbrugge et al. (2009) Combining radiotherapy with APO010 in cancer treatment. Clin Cancer Res. 15(6):2031-8.
Wenkel et al. (2000) Evidence that retinal pigment epithelium functions as an immune-privileged tissue. *Invest Ophthalmol Vis Sci* 41: 3467-3473.
Yu et al. (2013). Epigenetic signature and enhancer activity of the human APOE gene. *Hum Mol Genet.* 22(24):5036-47.
Zieger et al. (2014) CX3CL1 (Fractalkine) Protein Expression in Normal and Degenerating Mouse Retina: In Vivo Studies. *PloS One* 9: e106562.

The invention claimed is:

1. A method for treating retinal inflammation in a subject in need thereof, comprising administering to the subject an IL-6 inhibitor as an active ingredient, wherein said retinal inflammation comprises atrophic age-related macular degeneration (AMD) and retinitis pigmentosa and is not associated with neovascularization.

2. The method according to claim 1, wherein said IL-6 inhibitor comprises (i) an antagonist of IL-6 activity or (ii) an antagonist of IL-6 receptor.

3. The method according to claim 1, wherein said IL-6 inhibitor is administered intraocularly, or applied by topical ocular administration.

4. The method according to claim 1, wherein said IL-6 inhibitor is in a concentration from 5 mg/mL to 500 mg/mL.

5. The method according to claim 1, wherein said IL-6 inhibitor is an antibody recognizing IL-6, a soluble IL-6 receptor or an inhibitor of IL-6 translation.

6. The method according to claim 1, wherein said IL-6 inhibitor is an antibody recognizing IL-6R or an IL-6R binding peptide.

7. The method according to claim 1, wherein said IL-6 inhibitor is administered intraocularly by intravitreal injection.

8. The method according to claim 1, wherein said IL-6 inhibitor is an antibody recognizing IL-6, a soluble IL-6 receptor or an antibody recognizing IL-6R.

* * * * *